United States Patent
Mao et al.

(10) Patent No.: US 11,672,819 B2
(45) Date of Patent: Jun. 13, 2023

(54) POLYSACCHARIDE CARBON NANOGELS AND ANTICOAGULANTS AND ANTIOXIDANTS COMPRISING THE SAME

(71) Applicant: NATIONAL TAIWAN OCEAN UNIVERSITY, Keelung (TW)

(72) Inventors: Ju-Yi Mao, Keelung (TW); Chin-Ching Huang, Keelung (TW); Han-Jia Lin, Keelung (TW)

(73) Assignee: NATIONAL TAIWAN OCEAN UNIVERSITY, Keelung (TW)

( * ) Notice: Subject to any disclaimer, the term of this patent is extended or adjusted under 35 U.S.C. 154(b) by 26 days.

(21) Appl. No.: 17/169,637

(22) Filed: Feb. 8, 2021

(65) Prior Publication Data
US 2022/0249541 A1    Aug. 11, 2022

(51) Int. Cl.
| | |
|---|---|
| *A61K 31/734* | (2006.01) |
| *A61K 47/69* | (2017.01) |
| *A61K 47/52* | (2017.01) |
| *A61K 9/70* | (2006.01) |
| *A61P 7/02* | (2006.01) |

(52) U.S. Cl.
CPC .............. *A61K 31/734* (2013.01); *A61K 9/70* (2013.01); *A61K 47/52* (2017.08); *A61K 47/6953* (2017.08); *A61P 7/02* (2018.01)

(58) Field of Classification Search
CPC .. A61K 31/734; A61K 47/6953; A61K 47/52; A61K 9/70; A61P 7/02
See application file for complete search history.

(56) References Cited

PUBLICATIONS

W. Zhao, Y. Qi, Y. Wang, Y. Xue, P. Xu, Z. Li, and Q. Li. "Morphology and Thermal Properties of Calcium Alginate/Reduced Graphene Oxide Composites," Polymers 2018, 10, 990, 1-11. (Year: 2018).*

* cited by examiner

*Primary Examiner* — Michael P Cohen
(74) *Attorney, Agent, or Firm* — Amin, Turocy & Watson, LLP

(57) ABSTRACT

Provided is a nanogel exhibiting anticoagulation and antioxidation activities, including a graphene-like nanosheet and a polysaccharide, which are complexed to form a cross-linked supramolecular structure. Also provided is a method of preparing the nanogel, including carbonizing the polysaccharide by dry heating. By the heating process, at least a portion of the polysaccharide is conversed into the graphene-like nanosheet, thereby forming a graphene-like nanosheet-embedded phenolic-polysaccharide nanogel that has exceptional polyphenolic structure and high binding affinity toward thrombin. Further provided is a method of preventing or treating a disease or a condition susceptible to amelioration by anticoagulants or antioxidants by using the nanogel.

15 Claims, 27 Drawing Sheets

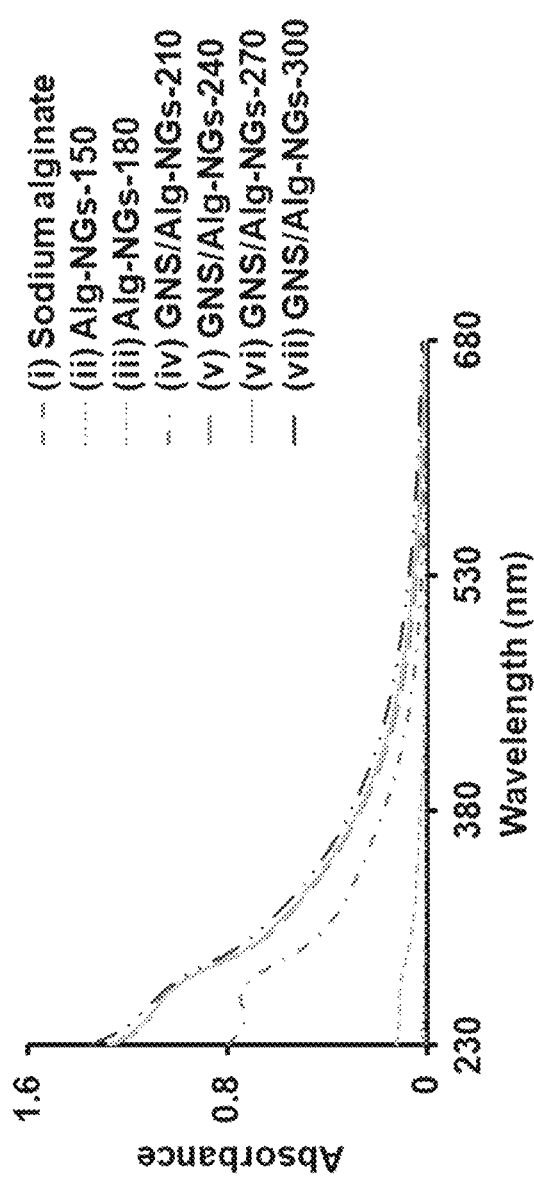
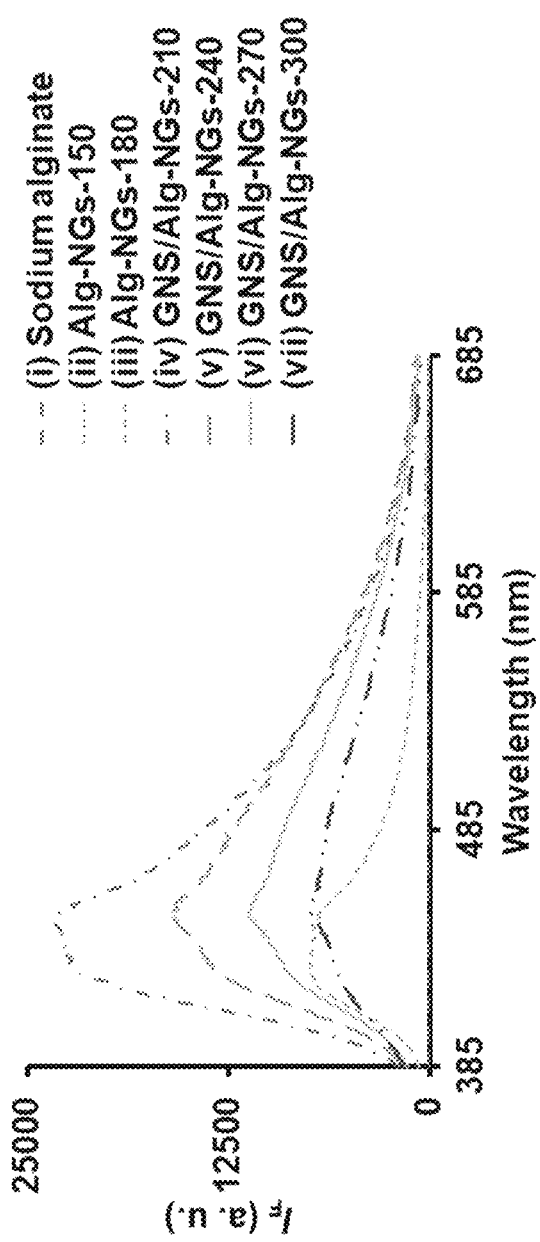
FIG. 5A
FIG. 5B

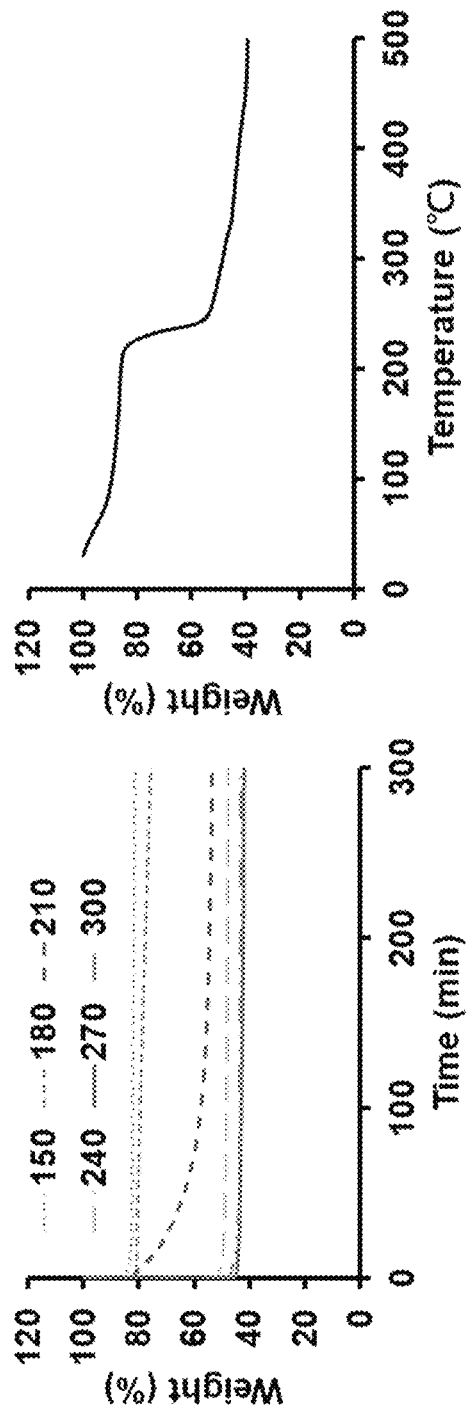
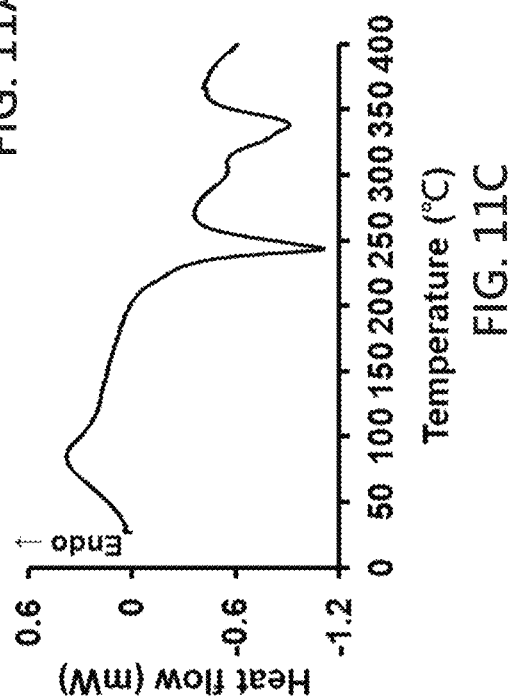
FIG. 11A
FIG. 11B
FIG. 11C

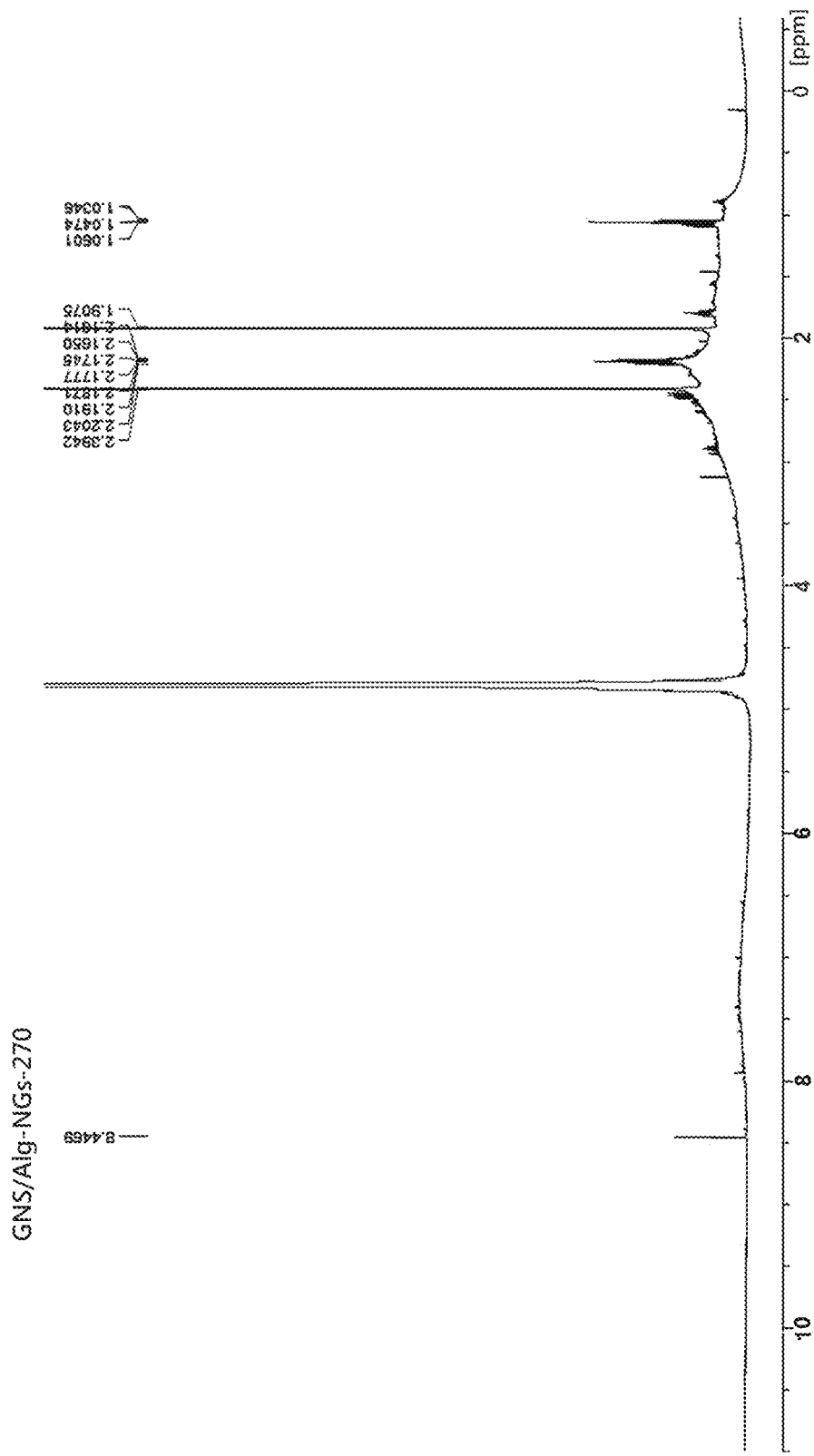

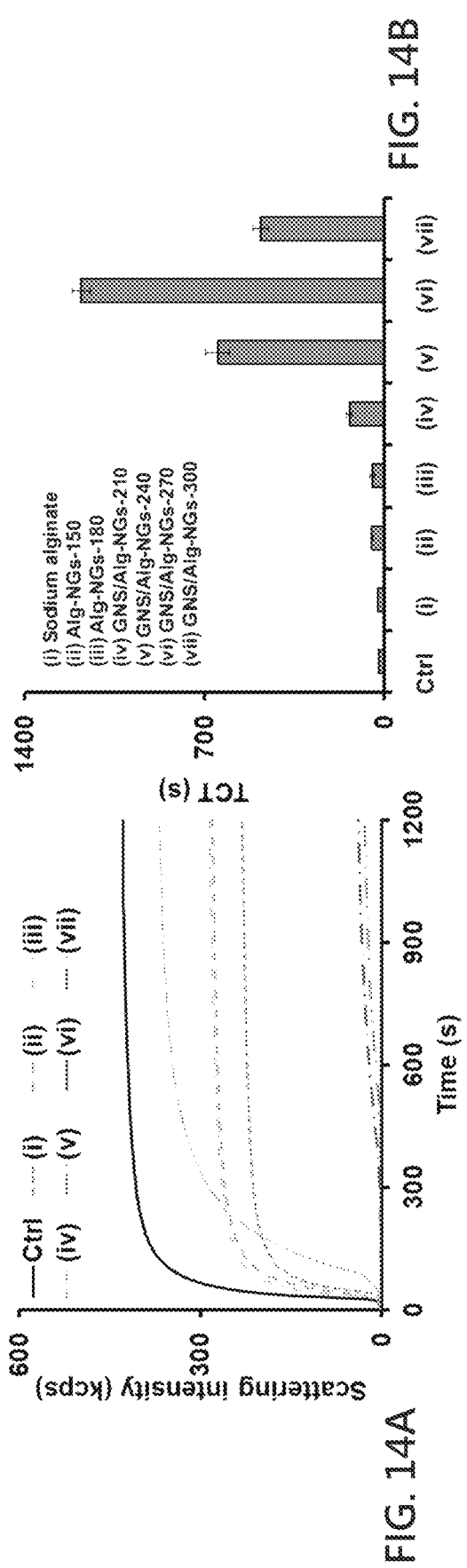
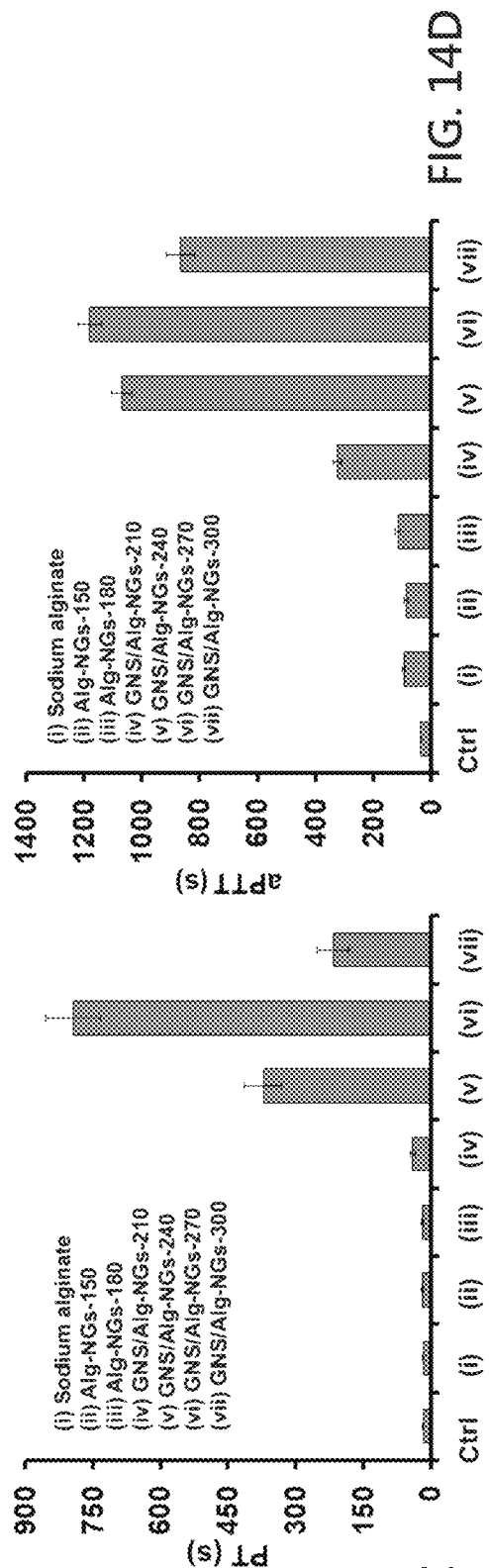
FIG. 14A  FIG. 14B  FIG. 14C  FIG. 14D

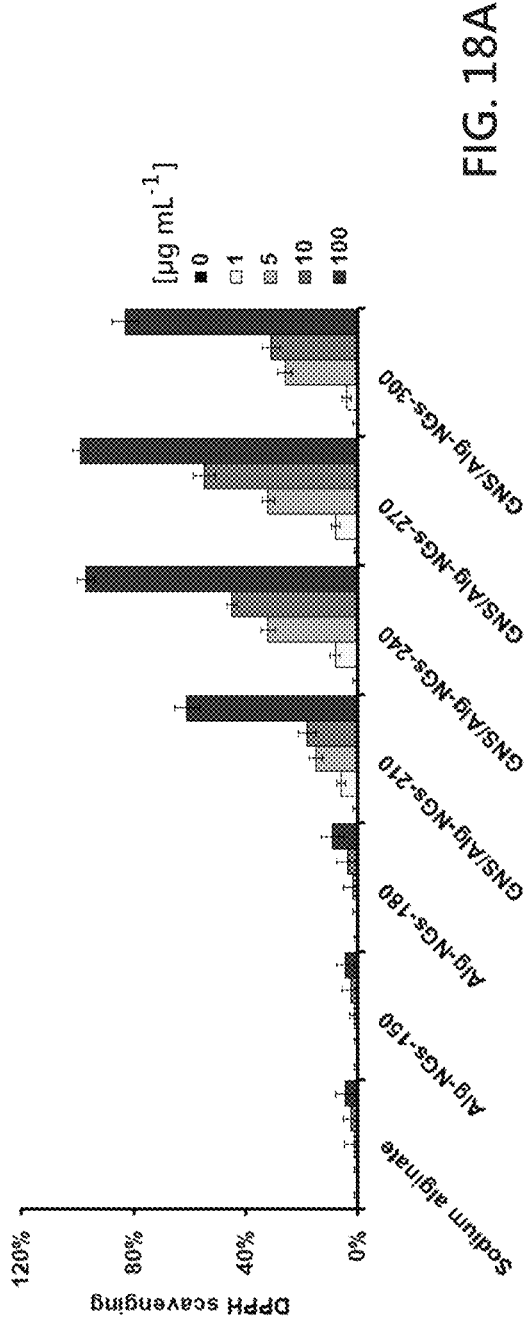
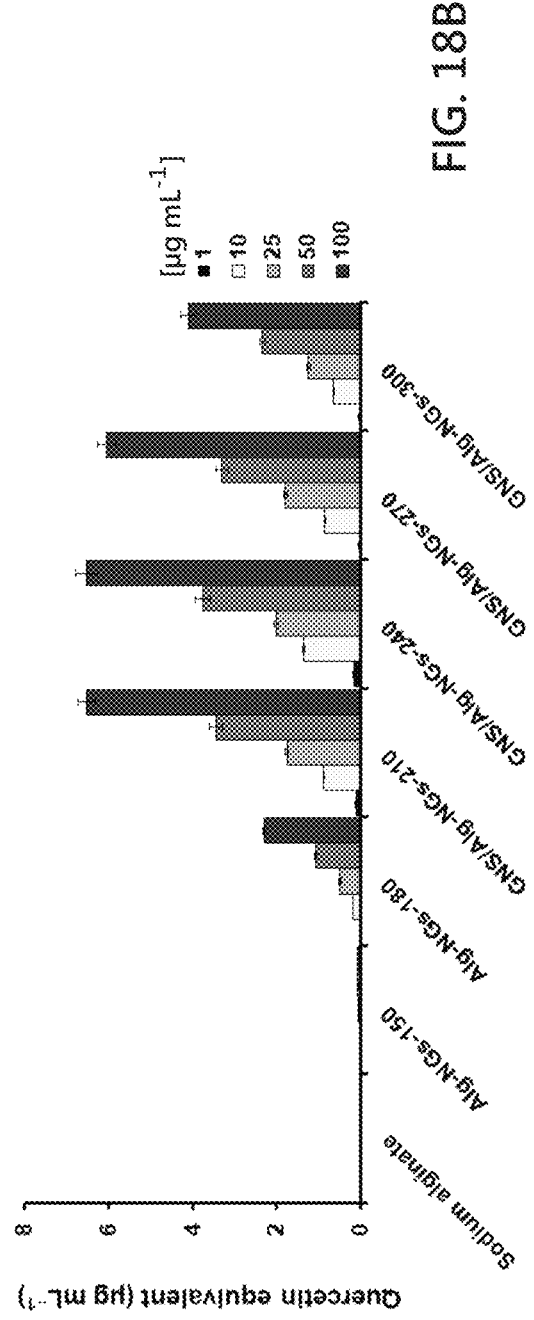
FIG. 18A
FIG. 18B

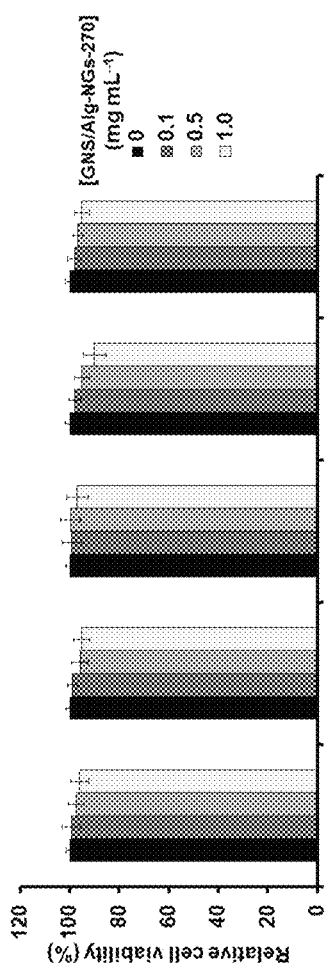
FIG. 22A
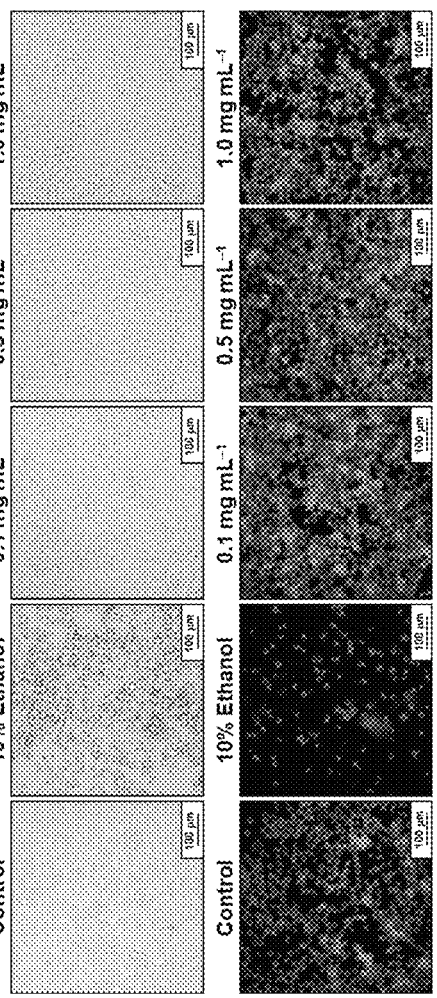
FIG. 22B
FIG. 22C
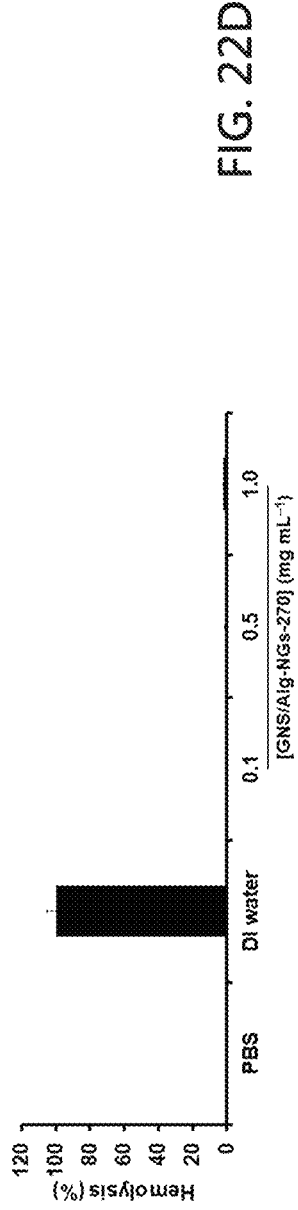
FIG. 22D

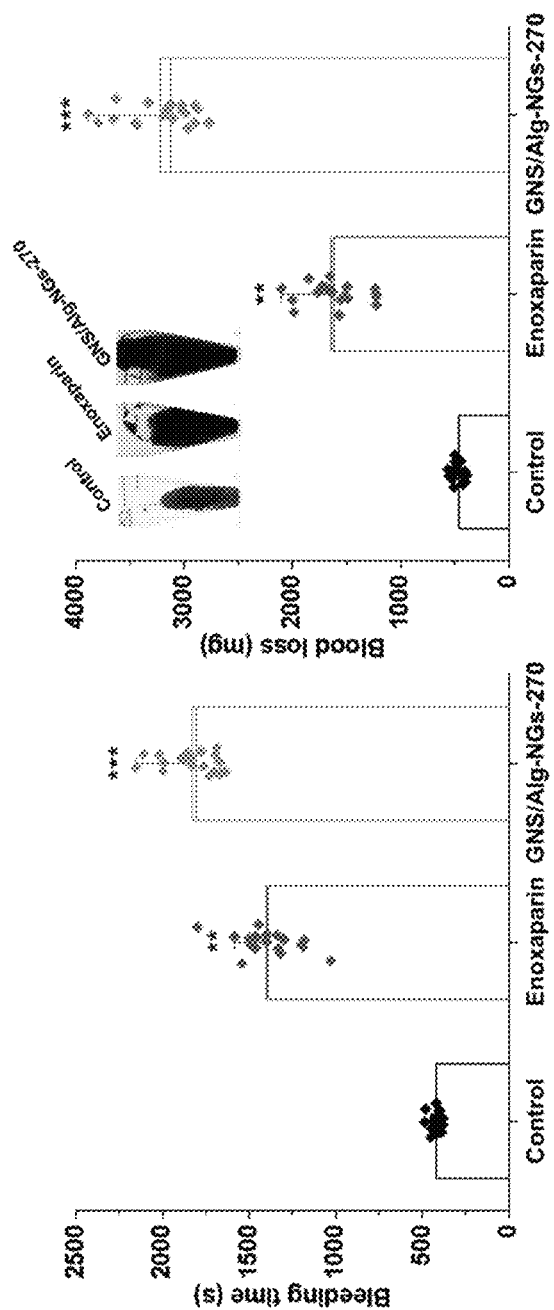
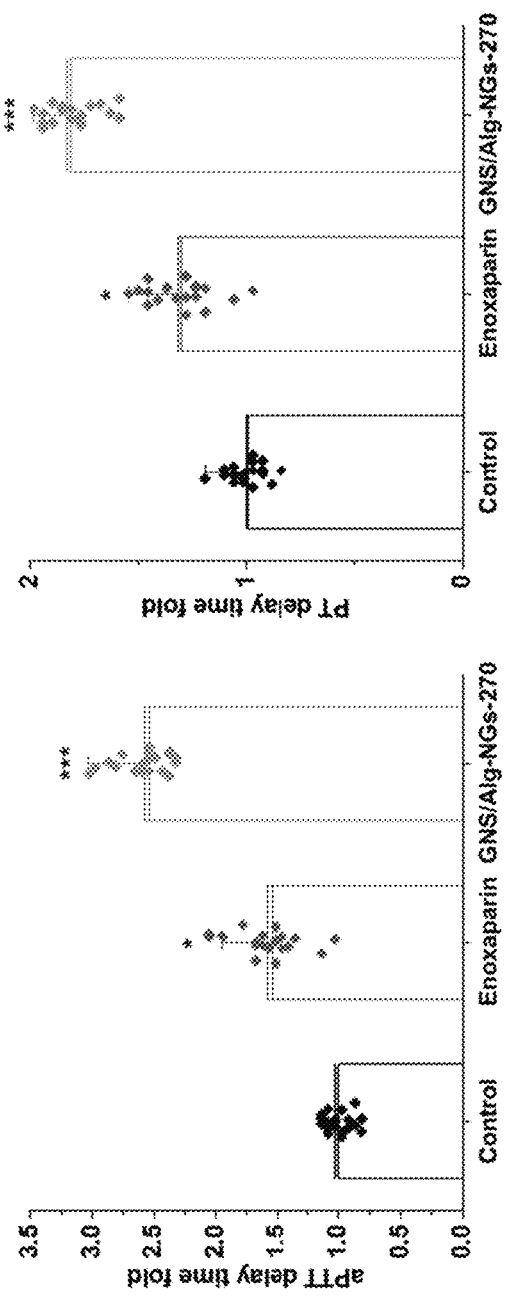
FIG. 23A
FIG. 23B
FIG. 23C
FIG. 23D

POLYSACCHARIDE CARBON NANOGELS AND ANTICOAGULANTS AND ANTIOXIDANTS COMPRISING THE SAME

BACKGROUND

1. Technical Field

The present disclosure relates to the field of nanopolymer engineering. More particularly, the present disclosure relates to phenolic-polysaccharide nanogels and the use thereof for anticoagulation and antioxidation applications. The present disclosure also relates to methods of preparing the phenolic-polysaccharide nanogels.

2. Description of Related Art

A blood clot is formed through a cascade of multifaceted reactions that occur upon the damage of blood vessels. This coagulation cascade is activated by several coagulation factors as well as thrombin, a serine protease formed through a sequential series of proteolytic processes of its zymogen prothrombin (*Thromb. Res.* 2014; 133: S139-S148). Thrombin catalyzes the polymerization of fibrinogen by cleaving small peptides (i.e., fibrinopeptide A and fibrinopeptide B) from two of its three subunits ($\alpha$ chain, $\beta$ chain, and $\gamma$ chain). Soluble dimeric fibrinogen with D and E domains is converted into insoluble fibrin through polymerization, which blocks the flow of blood and promotes hemostasis, thereby preventing major blood loss. However, thrombophilia, an abnormality of blood coagulation that can cause arterial and venous thrombosis, can cause severe damage to the lungs, brain, or heart, and may even result in pulmonary embolism, stroke, cardiac ischemia, and acute myocardial infarction (*Blood Transfus.* 2011; 9: 120-138). Therefore, it is vital to effectively prevent and treat abnormal thrombosis. Typically, treatment involves the prevention of vascular embolism by interfering with the production of one or more coagulation factors in the coagulation pathway and/or reducing platelet aggregation, thereby avoiding the formation of blood clots within blood vessels and reducing thrombosis. Most anticoagulants act by inhibiting different coagulation factors, which are categorized as direct inhibitors, indirect inhibitors, and vitamin K antagonists (*Thromb. Haemost.* 2015; 113: 931-942). Vitamin K antagonist such as warfarin acts through interfering with vitamin K epoxide reductase, which catalyzes the hepatic carboxylation of vitamin K-dependent coagulation factors (e.g., factors II, VII, IX, and X). Direct thrombin inhibitors (DTIs), such as argatroban, dabigatran, and bivalirudin, directly inhibit thrombin activity. Heparin and low-molecular-weight heparins, such as enoxaparin, fondaparinux, and apixaban, are widely used indirect anticoagulants that mainly function by inhibiting Factor Xa (*Drug Discov. Today* 2010; 15: 1058-1069). However, the most used anticoagulants, warfarin and heparin, have significant limitations, including their narrow therapeutic window, long half-life, numerous drug interactions, and negative side effects (e.g., bleeding, nausea, and nephrotoxicity). These limitations of heparins and warfarin have, therefore, inspired the development of new anticoagulant agents.

Natural polyphenol molecules that consist of multiples of phenol structural units are widely distributed in fruits, vegetables, seeds, and various species of algae. They possess anticancer, antidiabetic, anti-inflammatory, antioxidant, and anticoagulation functionalities (*Molecules* 2016; 21: 708; *Crit. Rev. Food Sci. Nutr.* 2016; 56: 419-444; *Nutrients* 2016; 8: 552). For example, Shobharani et al. reported that the purified extract from *Sargassum* sp., which contains polysaccharide and polyphenol, has anticoagulant properties (*Int. J. Biol. Macromol.* 2014; 65: 542-548). Bijak et al. found the polyphenol-rich extracts from black chokeberry and grape seeds to have an antithrombin effect (*Phytother. Res.* 2013; 27(1): 71-76), while Malinowska et al. reported that the above extracts have the potential to prevent platelet activation and cardiovascular events owing to their anticoagulation activity (*Eur. J. Nutr.* 2013; 52(3): 1049-1057). Prior to these studies, a series of natural flavonoids containing different phenol or hydroxyl groups at phenyl rings (A and B) and heterocyclic ring (C) was systematically studied for the inhibition of thrombin. It was found that the number of phenol groups and their positions involve in their anticoagulation activity (*Thromb. Res.* 2010; 126: e365-e378). However, natural polyphenolic acid compounds suffer from stability issues, plus their low abundance, and complex extraction and purification processes makes them even more expensive.

SUMMARY

In view of the foregoing, the present disclosure provides a bioinspired and eco-friendly approach for the one-pot synthesis of nanogels from cost-effective and easily available polysaccharides without needing to employ any catalyst and hazardous solvents.

In one aspect, the present disclosure provides a phenolic-polysaccharide nanogel having an anticoagulation activity and an antioxidation activity. In at least one embodiment, the nanogel comprises a graphene-like nanosheet and a polysaccharide, wherein the graphene-like nanosheet is complexed with the polysaccharide to form a cross-linked supramolecular structure.

In at least one embodiment, the graphene-like nanosheet comprises a carbonization product of at least a portion of the polysaccharide. In some embodiments, the carbonization product is formed by dry heating the polysaccharide.

In at least one embodiment, the polysaccharide is a salt of alginic acid, such as sodium alginate, calcium alginate, magnesium alginate, and any combination thereof.

In at least one embodiment, the polysaccharide has a free end and a fixed end, and the fixed end of the polysaccharide is bonded to the surface of the graphene-like nanosheet.

In at least one embodiment, the cross-linked supramolecular structure has a functional group on the surface thereof. In some embodiments, the functional group is selected from the group consisting of hydroxyl, ester, phenol, carboxyl and any combination thereof.

In at least one embodiment, the phenolic-polysaccharide nanogel has a hydrodynamic diameter ranging from 20 nm to 490 nm, e.g., a hydrodynamic diameter with a lower limit not less than 20 nm or with an upper limit not greater than 490 nm. In some embodiments, the phenolic-polysaccharide nanogel has a hydrodynamic diameter ranging from 40 nm to 450 nm, e.g., about 45 nm, about 50 nm, about 60 nm, about 80 nm, about 100 nm, about 120 nm, about 150 nm, about 180 nm, about 200 nm, about 225 nm, about 250 nm, about 275 nm, about 300 nm, about 350 nm, about 400 nm, about 425 nm, about 450 nm and about 460 nm.

In at least one embodiment, the phenolic-polysaccharide nanogel has a zeta potential ranging from −26.5 mV to −47.5 mV, e.g., a zeta potential with a lower limit not less than −47.5 mV or with an upper limit not greater than −26.5 mV. In some embodiments, the phenolic-polysaccharide nanogel has a zeta potential ranging from −30 mV to −45 mV, e.g., about −32.5 mV, about −35 mV, about −37.5 mV, about −40 mV, and about −42.5 mV.

In at least one embodiment, the graphene-like nanosheet has lattice planes of the (100) and (112) facets.

In one aspect, the present disclosure also provides a method of preparing the above phenolic-polysaccharide nanogels, comprising carbonizing the polysaccharide by dry heating.

In at least one embodiment, the dry heating is performed at a temperature ranging from 150° C. to 300° C., e.g., a temperature with a lower limit not less than 150° C. or with an upper limit not greater than 300° C. In some embodiments, the heating temperature ranges from 180° C. to 300° C., e.g., about 190° C., about 200° C., about 210° C., about 220° C., about 230° C., about 240° C., about 250° C., about 260° C., about 270° C., about 280° C. and about 290° C.

In another aspect, the present disclosure provides a composition for use in anticoagulation. The composition comprises any one of the above phenolic-polysaccharide nanogels and a pharmaceutically acceptable vehicle thereof.

In a further aspect, the present disclosure provides a composition for use in antioxidation. The composition comprises any one of the above phenolic-polysaccharide nanogel and a pharmaceutically acceptable vehicle thereof.

In a yet further aspect, the present disclosure provides a method for preventing or treating a disease or a condition susceptible to amelioration by an anticoagulant or an antioxidant in a subject in need thereof, comprising administering to the subject any one of the above medical compositions.

In at least one embodiment, the disease or the condition susceptible to amelioration by anticoagulants or antioxidants may be thrombophilia, vascular thrombosis, pulmonary embolism, cardiac ischemia, ischemic stroke, cryptogenic stroke, embolic stroke of an undetermined source, myocardial infarction, pulmonary hypertension, or asthma.

The nanogels provided in the present disclosure are graphene-like nanosheet-embedded polyphenolic-alginate nanogels (hereinafter referred to as "GNS/Alg-NGs"), which are formed through polycondensation (cross-linking), carbonization, and in situ passivation during the dry heating of polysaccharide (e.g., sodium alginate), as illustrated in FIG. 1. The GNS/Alg-NGs display high aqueous solubility, biocompatibility, and superior anticoagulation properties, which make them a potential candidate for the treatment of thrombotic disorders. The GNS/Alg-NGs display high anticoagulation activities as a result of their strong affinity for thrombin as well as inhibition of other coagulation factors such as factor V, factor VII, factor XI, and factor XII. Furthermore, the formation of phenol groups on the partial carbonized structures of GNS/Alg-NGs involves in their anticoagulation activity. The multiple mechanisms mediating the anticoagulation activity of GNS/Alg-NGs make them be an effective anticoagulant for the prevention of abnormal thrombus formation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure can be more fully understood by reading the following descriptions of the embodiments, with reference made to the accompanying drawings.

FIGS. 5A and 5B show the UV-vis absorption and the fluorescence spectra of sodium alginate, Alg-NGs, and GNS/Alg-NGs, respectively.

FIGS. 11A to 11C show the results of thermogravimetric analysis (TGA) and differential scanning calorimetry (DSC) of sodium alginate. FIG. 11A shows the constant TGA data of sodium alginate at 150° C. to 300° C. 150: Alg-NGs-150; 180: Alg-NGs-180; 210: GNS/Alg-NGs-210; 240: GNS/Alg-NGs-240; 270: GNS/Alg-NGs-270; 300: GNS/Alg-NGs-300. FIG. 11B shows the temperature-dependent TGA of sodium alginate. FIG. 11C shows the DSC curve of sodium alginate.

FIGS. 13A to 13C show the $^1$H-nuclear magnetic resonance (NMR) spectra of sodium alginate (FIG. 13A) and GNS/Alg-NGs-270 (FIGS. 13B and 13C) at the concentration of 50 mg/mL in deuterated water ($D_2O$) at 298 K.

FIGS. 14A to 14D show the in vitro anticoagulation of GNS/Alg-NGs, in which FIG. 14A shows the scattering light intensity, FIG. 14B shows the thrombin clotting time (TCT), FIG. 14C shows the prothrombin time (PT), and FIG. 14D shows the activated partial thromboplastin time (aPTT). Ctrl: control.

FIGS. 18A and 18B show the comparison of antioxidant activity of sodium alginate, Alg-NGs, and GNS/Alg-NGs by DPPH scavenging assay and Folin-Ciocalteu assay, respectively.

FIGS. 22A to 22D show the biocompatibility of GNS/Alg-NGs by cell viability, bright field, and fluorescent images of live/dead cells, and hemolysis assay, respectively.

FIGS. 23A to 23D show the anticoagulation effect of GNS/Alg-NGs in the animal model, in which FIG. 23A shows the rat tail bleeding time, FIG. 23B shows the blood loss ex vivo, FIG. 23C shows the results of aPTT assay, and FIG. 23D shows the results of prothrombin time (PT) assay.

DETAIL DESCRIPTION OF THE EMBODIMENTS

Figure 1A:
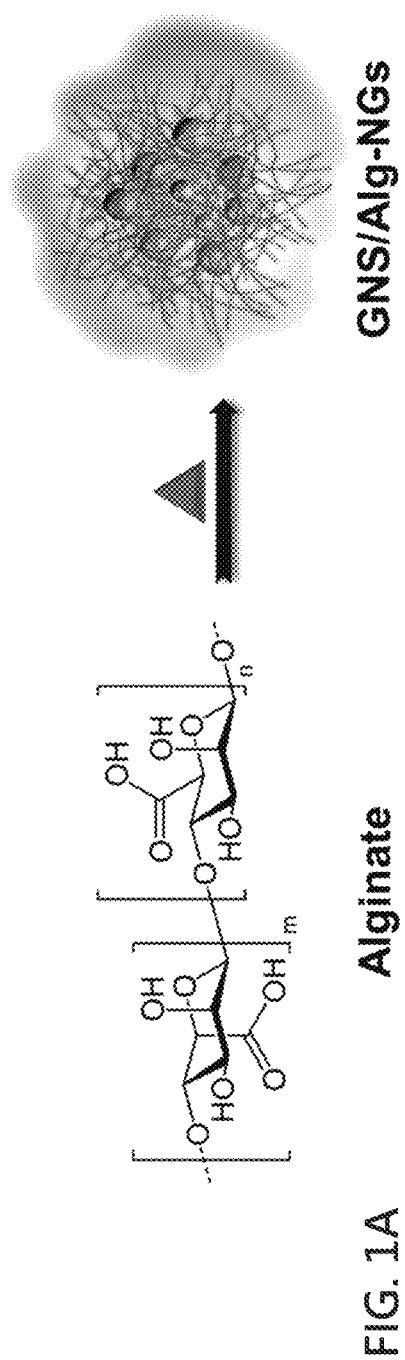
FIGS. 1A and 1B are schematic diagrams illustrating the preparation and anticoagulation applications of GNS/Alg-NGs, respectively.
Figure 1B:
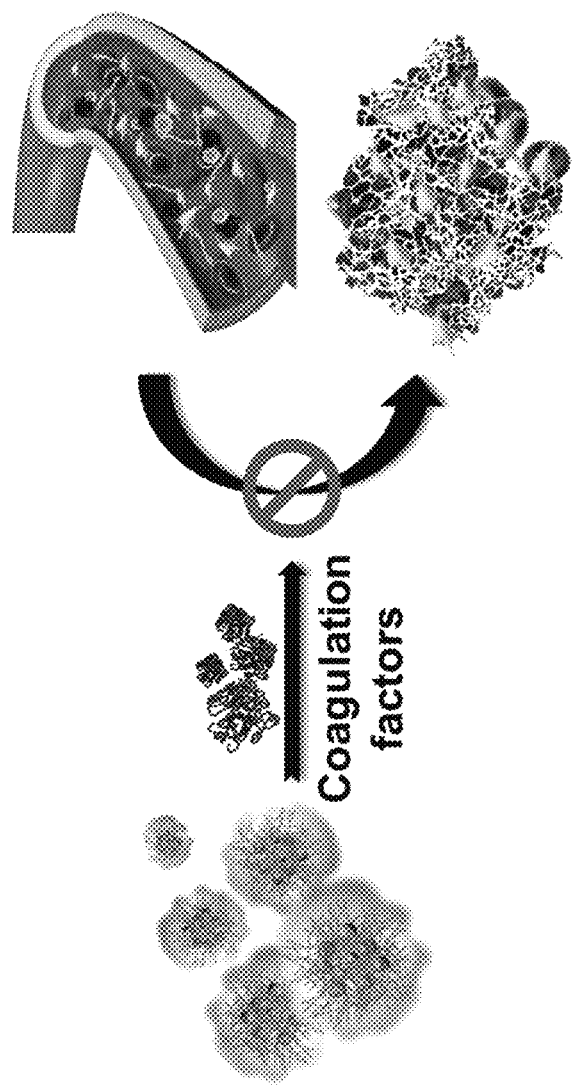

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the following examples for carrying out this disclosure without contravening its scope, for different aspects and applications.

It is further noted that, as used in this disclosure, the singular forms "a," "an," and "the" include plural referents, unless expressly and unequivocally limited to one referent. The term "or" is used interchangeably with the term "and/or," unless the context clearly indicates otherwise.

As used herein, the term "comprising" or "comprises" is used in reference to compositions, methods, and respective component(s) thereof, which are included in the present disclosure, yet open to the inclusion of unspecified elements.

The present disclosure is directed to a phenolic-polysaccharide nanogel useful for being an anticoagulant or an antioxidant. The phenolic-polysaccharide nanogel comprises a graphene-like nanosheet and a polysaccharide, wherein the graphene-like nanosheet comprises a carbonization product of at least a portion of the polysaccharide, and is complexed with the polysaccharide to form a cross-linked supramolecular structure. In some embodiments, the polysaccharide used for the preparation of the nanogels may be a salt of alginic acid.

Alginate is composed of β-(1→4)-linked D-mannuronic acid (M) and α-(1→4)-linked L-guluronic acid (G) units. Sodium alginate has already been found of widespread use in food industry, pharmaceuticals, and many biomedical applications (e.g., wound dressing, drug delivery, and immunotherapy) due to its high biocompatibility, low cost, and mild gel-forming capacity by the addition of divalent cations (e.g., $Mg^{2+}$ and $Ca^{2+}$). However, alginate, which has linearly configured uronans (polyuronic acids) without sulfate and sulfonate groups, generally exhibits negligible anticoagulation activity. Therefore, chemical sulfation is a common approach to improve the anticoagulation efficiency of alginates (*Carbohydr. Polym.* 2011; 83: 1797-1803; *Biomacromolecules* 2014; 15: 2744-2750). Nevertheless, the improvement is limited because of the unstable biological activity and the requirement of organic solvents during the sulfation process. In addition, chemically modifying polysaccharides are complicated, and the sulfated polysaccharides are easily degraded (*Molecules* 2017; 22: 778).

In the present disclosure, the phenolic-polysaccharide nanogels are prepared by dry heating alginate, so as to obtain a carbonization product. The bottom-up synthesis of carbon quantum dots (CQDs) and carbonized polymer dots (CPDs) results in the formation of aromatic domains with diverse functional groups during their thermal synthesis processes.

Accordingly, in at least one embodiment, the cross-linked supramolecular structure formed in the nanogels of the present disclosure has at least one functional groups on the surface thereof, such as hydroxyl, ester, phenol, and carboxyl, so as to render properties for bio-applications to the nanogels.

In some embodiments, a medical composition for use in treating a disease or a condition susceptible to amelioration by anticoagulants or antioxidants is provided. The medical composition comprises the nanogel mentioned above and a pharmaceutically acceptable vehicle thereof.

As used herein, the term "pharmaceutically acceptable vehicle" refers to a pharmaceutically acceptable material, composition, or carrier, such as diluents, disintegrating agents, binders, lubricants, glidants, and surfactants, which do not abrogate the biological activity or properties of the active ingredient (e.g., the nanogel used herein), and is relatively non-toxic; that is, the vehicle may be administered to a subject without causing an undesirable biological effect or interacting in a deleterious manner with any of the components of the medical composition in which it is contained.

As used herein, the terms "treat," "treating," and "treatment" refer to acquisition of a desired pharmacologic and/or physiologic effect, e.g., alleviating or abrogating a disorder, disease, or condition, or one or more of the symptoms associated with the disorder, disease, or condition, or alleviating or eradicating the cause(s) of the disorder, disease, or condition itself. The effect may be prophylactic in terms of completely or partially preventing a disease or symptom thereof or may be therapeutic in terms of completely or partially curing, alleviating, relieving, remedying, or ameliorating a disease or an adverse effect attributable to the disease or symptom thereof.

As used herein, the terms "prevent," "preventing," and "prevention" refer to inclusion of a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, the term "subject" refers to a mammal, such as a human, but can also be another animal such as a domestic animal (e.g., a dog, a cat, or the like), a farm animal (e.g., a cow, a sheep, a pig, a horse, or the like) or a laboratory animal (e.g., a monkey, a rodent, a murine, a rabbit, a guinea pig, or the like). The term "patient" refers to a "subject" who is suspected to be, or afflicted with a disease or condition.

Many examples have been used to illustrate the present disclosure. The examples below should not be taken as a limit to the scope of the present disclosure.

EXAMPLES

Materials and Methods

The materials and methods used in the following Examples 1-6 were described in detail below. The materials used in the present disclosure but unannotated herein were commercially available.

(1) Characterization of Graphene-Like Nanosheet-Embedded Polyphenolic-Alginate Nanogels (GNS/Alg-NGs)

The particle size and morphology of the GNS/Alg-NGs were analyzed using a Tecnai G2 F20 S-TWIN (Philips/FEI, Hillsboro, Oreg., USA) transmission electron microscopy (TEM) system operating at 200 kV. The GNS/Alg-NGs were carefully deposited on 300-mesh carbon-coated Cu grids at ambient temperature.

The hydrodynamic diameters and zeta potential ($\zeta$-potential) of untreated sodium alginate and GNS/Alg-NGs in 5 mM sodium phosphate buffer (pH 7.4) were determined by dynamic light scattering (DLS, Zetasizer Nano ZS90, Malvern Instruments, Malvern, UK).

The photoluminescence (PL) spectra of the GNS/Alg-NGs in 5 mM sodium phosphate buffer (pH 7.4) were recorded using a monochromatic microplate spectrophotometer (Synergy 4 Multi-Mode; BioTek Instruments, Winooski, Vt., USA). The fluorescence quantum yields (QYs) of the GNS/Alg-NGs were determined by comparison with that of quinine sulfate standard (QY=54% in 0.1 M $H_2SO_4$).

Samples for X-ray diffraction (XRD) were prepared by depositing the GNS/Alg-NGs solution onto a silicon wafer, followed by drying at room temperature. XRD measurements were carried out at room temperature with an X-ray diffractometer (D/MAX 2200 VPC, Rigaku, Sendagaya, ShibuyaKu, Tokyo, Japan) with the Cu $K_{\alpha 1}$ line ($\lambda$=1.54 Å, energy=8.8 keV). X-ray photoelectron spectroscopy (XPS) was performed using an ESCALAB 250 spectrometer (VG Scientific, East Grinstead, England, UK) with Al K$\alpha$ X-ray radiation as the X-ray source for excitation. Elemental analysis (EA) of the GNS/Alg-NGs was performed using a Vario EL cube analyzer (Elementar, Hanau, Germany) for C, H, and O.

Binding energies were corrected using the C1s peak at 284.6 eV as the standard. A Fourier transform infrared spectrometer (FT-IR, FT/IR-6100, JASCO, Easton, Md., USA) in transmission mode in the range of 500 $cm^{-1}$ to 4,000 $cm^{-1}$ with 16 scans was used to analyze possible functional groups existing in the GNS/Alg-NGs.

High-purity nitrogen was used for purging during the Fourier-transform infrared spectroscopy (FT-IR) measurements to minimize the interference from water vapor. Thermogravimetric analysis (TGA) and differential scanning calorimetry (DSC) were conducted using a TGA instrument (Q500, TA Instruments, New Castle, Del., USA) and a TA 2010 instrument (TA Instruments) in an air atmosphere (60 mL/min), respectively.

The viscosity was measured with a cone plate (cone spindle: CPA-40Z) viscometer (Brookfield, model DV1MLV, Middleboro, Mass., USA). Cyclic voltammetry (CV) was performed in a PBS solution by using a three-electrode system composed of a glassy carbon electrode (GCE) as the working electrode, a platinum electrode as the counter electrode, and a saturated calomel electrode (SCE) as a reference electrode. Cyclic voltammetry was conducted using a potentiostat/galvanostat Autolab PGSTAT204 (Metrohm Autolab, Utrecht, the Netherlands) within the voltage range of −1.2 V to 1.2 V. The $^1$H-NMR spectrum was recorded using the Avance 600 MHz spectrometer (Bruker, Billerica, Mass., USA) and referenced to the solvent signals.

(2) Agarose Gel Retardation

Sodium alginate and the obtained GNS/Alg-NGs samples (5 mg/mL; 15 μL) were separately mixed with 10% glycerol, and then analyzed by gel electrophoresis in 1.0% agarose gel and 40 mM Tris-acetate buffer/1 mM ethylenediaminetetraacetic acid (TAE buffer, pH 8.0) at 100 V for 30 min. The gel was externally stained by the positively charged methylene blue (0.1 mg/mL, 150 mL) after electrophoresis and destained in TAE buffer (pH 8.0) for 30 min

(3) Thrombin Clotting Time (TCT) Assay

For the TCT assay, the human plasma was donated from healthy individuals at Mackay Memorial Hospital (Taipei, Taiwan) as per the rules and regulations of the research ethics committee of the institution. Further, two-fold-diluted human plasma was incubated with GNS/Alg-NGs or other inhibitors (final concentration 500 μg/mL) at 37° C. in 475 μL of phosphate-buffered saline (PBS) for 5 min. Then, 25 μL of 15 nM thrombin was added to initiate the clotting cascade. The thrombin activity and clot formation were monitored by measuring the intensity of the scattered light at 650 nm using an FP-6500 spectrophotometer (JASCO, Tokyo, Japan).

(4) Rat-Tail Bleeding Assay and Prothrombin Time and Activated Partial Thromboplastin Time Assays To evaluate the practicality of GNS/Alg-NGs, in vivo rat-tail incision bleeding model assays were carried out on male Sprague-Dawley rats (200 g to 250 g). Animal experiments were performed with permission from the Institutional Animal Care and Use Committee of the National Laboratory Animal Center, Taipei, Taiwan (IACUC Approval Number: 105021). Healthy rats were anesthetized, and then dosed by intravenous injection with enoxaparin and GNS/Alg-NGs-270 in PBS at a dose of $5 \times 10^{-1}$ mg/kg, followed by waiting for 5 min. Then, the rat-tail tip was cut (4 mm) and immersed in a physiological buffer. The bleeding time was noted as the time at which bleeding stopped. Statistical analysis was performed using the Student's t-test. The probability of rat survival was calculated by the Kaplan-Meier method.

For the prothrombin time (PT) assay in human plasma samples, sodium alginate or GNS/Alg-NGs (0.5 mg/mL, 100 μL) were separately incubated with 200 μL of human plasma at 37° C. for 3 min, followed by the addition of 200 μL of the PT reagent to initiate the extrinsic clotting cascade. Coagulation was monitored by measuring the intensity of scattered light until the signals reached saturation. For the activated partial thromboplastin time (aPTT) determinations, 160 μL of human plasma was incubated with 240 μL (0.5 mg/mL) of each inhibitor (sodium alginate or GNS/Alg-NGs) at 37° C. for 5 min. Then, 100 μL of the aPTT reagent was added, followed by incubation for 3 min. To initiate the intrinsic clotting cascade, 100 μL of prewarmed $CaCl_2$ solution was added. The aPTT was noted as the time at which the intensity of the scattered light reached a plateau. To calculate the PT and aPTT, the end time was chosen as the point at which the scattered light signal intensity was halfway between the lowest and maximal values.

For ex vivo PT and aPTT measurements, enoxaparin and GNS/Alg-NGs in PBS were intravenously administered to male Sprague-Dawley rats (200 g to 250 g) at a dose of 1.0 mg/kg, followed by waiting for 30 min. The rats were then anesthetized, and their whole blood (4.5 mL) was collected by cardiac puncture and transferred into plastic tubes containing sodium citrate (0.5 mL, 3.2%).

(5) Determination of the Dissociation Constant of Thrombin with GNS/Alg-NGs

The dissociation constant ($K_d$) for the interaction of GNS/Alg-NGs with thrombin was determined to understand the anticoagulant properties of the GNS/Alg-NG against thrombin activity. Briefly, aliquots of GNS/Alg-NGs solution (0.1 mg/mL) with different concentrations of thrombin (0 to 800 pM) were added to PBS containing bovine serum albumin (BSA, 100 µM) and incubated for 30 min to allow the interaction between thrombin and GNS/Alg-NGs. To further separate the thrombin-GNS/Alg-NGs and free thrombin, the mixture (40 µL) was added into a size exclusion chromatography (SEC) column (Sephacryl S-200 HR, GE Healthcare Chicago, Ill., USA) with a bed volume of 1.0 mL. The sample solution of the fraction was eluted 7 times with 200 µL of a PBS solution. The fractions 4 to 7 with free thrombin were collected, estimated to fibrinogen-modified gold nanoparticles (Au NPs; 56 nm) solution, and then the Kd value was calculated according to a previously published method (*Biosens. Bioelectron.* 2010; 25: 1922-1927). The saturation binding data were processed using the Scatchard equation below to examine the binding properties:

$$N_{Thrombin}/[\text{Free-Thrombin}]=N_{max}/K_d=N_{Thrombin}/K_d$$

$N_{Thrombin}$ is the number of thrombin molecules bound to GNS/Alg-NGs at equilibrium, [Free-Thrombin] is the unbound thrombin concentration at equilibrium, $N_{max}$ is the apparent maximal number of binding sites, and $K_d$ is the dissociation constant. The values $1/K_d$ was obtained from the slope of the plot of $N_{Thrombin}/[\text{Free-Thrombin}]$ against $N_{Thrombin}$, respectively.

(6) The Coagulation Factor Activity Test

The activity of coagulation factors (II, V, VII, X, XI, XII) was determined by a Sysmex CS-2500 System (Siemens Healthineers, Erlangen, Germany). The GNS/Alg-NGs-270 (2.0 mg/mL; 100 µL) and human plasma (900 µL) were mixed for analysis. Except for the measured clotting factor, the remaining clotting factors were added in excess, and then the activation agents were added (20 µL) directly before analysis. The clotting time of the various factors was determined by the detection of transmitted light (absorbance) at 660 nm. The raw data was then inputted into a mathematical algorithm from the instrument to determine the solidification time.

(7) 2,2-diphenyl-1-picrylhydrazyl (DPPH) Radical Scavenging Activity

To measure the radical scavenging activity of GNS/Alg-NGs, various concentrations of untreated sodium alginate or GNS/Alg-NGs (1 µg/mL to 100 µg/mL) were added to a DPPH solution (50 µM, diluted in ethanol (EtOH)) in a mixing solution of 50% PBS and 50% EtOH, and then reacted for 30 min at room temperature. The decrease in the solution absorbance was measured at 525 nm. The percentage DPPH radical scavenging activity was calculated using the following formula:

$$\text{DPPH radical scavenging activity (\%)}=[(A_0-A_1)/A_0 \times 100]$$

where $A_0$ and $A_1$ are the absorbance values in the absence and presence of alginate or GNS/Alg-NGs, respectively.

(8) Folin-Ciocalteu Assay

The total phenolic content of the GNS/Alg-NGs was measured by using the Folin-Ciocalteu reagent. Briefly, 40 µL of GNS/Alg-NGs were mixed with Folin-Ciocalteu reagent (240 µL) for 0.5 hours (h), and 120 µL of sodium carbonate (7.5%, w/v) was added after 0.5 h. The absorbance was then measured at 760 nm after incubation at 25° C. for an additional 0.5 h. Results were expressed as standard quercetin equivalents (µg of quercetin/µg of GNS/Alg-NGs). The Folin-Ciocalteu assay was based on the transfer of electrons from phenolic compounds in a basic solution to phosphomolybdic/phosphotungstic acid to form blue complexes [$(PMoW_{11}O_{40})^{4-}$], which were quantitated by monitoring the absorbance at 760 nm. However, the Folin-Ciocalteu assay was not only sensitive to phenolic compounds but also many reducing agents. Thus, this assay could be employed to measure the total reducing capacity of the sample.

(9) Thromboelastography

Thromboelastography (TEG; thromboelastograph analyzer, Haemoscope Corporation, Niles, Ill., USA) was employed to evaluate the anticoagulation efficiency of sodium alginate, GNS/Alg-NGs-270, and the well-known sulfated polysaccharide with prominent anticoagulant activity, fucoidan, in whole blood clots through the viscoelastic development of thrombin-mediated fibrin polymerization and platelet activation.

Blood samples were collected from a healthy volunteer (24 years old) into tubes containing sodium citrate (3.2%). Blood collection at Mackay Memorial Hospital (MMH; Taipei, Taiwan) was performed in compliance with the relevant laws. Plain disposable plastic TEG cups (Haemonetics) were equilibrated at 37° C. before the experiments. On the thrombin-activated TEG assay, sodium alginate, GNS/Alg-NGs-270, fucoidan, or other commercial drugs (0.1 mg/mL to 0.5 mg/mL, 52 µL) in a physiological buffer was mixed with 288 µL of whole blood and incubated in a TEG cup at 37° C. for 10 min. Then, the thrombin solution (15 nM, 20 µL) was added to the TEG cup to initiate whole-blood coagulation and then monitored for 30 min. Likewise, the same concentration of samples was mixed with the same amount of whole blood (288 µL) and kaolin solution (14 µL), then incubated in a TEG cup at 37° C. for 10 min on the kaolin-activated TEG assay. Then, the calcium chloride solution ($CaCl_2$, 14 µL) was added to the TEG cup to initiate whole-blood coagulation and then monitored for 30 min. The clot formation at 37° C. was measured with the thromboelastography analyzer until a stable clot had formed or one hour had passed. The degree of motion was set to 4.75° around a fixed plastic pin to measure the clot reaction time (R) (minutes), clot kinetics (K, time from clot formation to the time that the amplitude reaches 20 mm) (minutes), α-angle (α, formed by the slope from the R value to the K value representing the acceleration of fibrin build-up and cross-linking) (degree) and maximum amplitude (MA, amplitude measured at the widest point of TEG tracing). The lag time, α angle, and maximum amplitude were automatically calculated by the TEG Analytical software (TAS) version 4.2.3 (Haemonetics).

(10) In vitro Cytotoxicity Assay

For determining in vitro cytotoxicity of GNS/Alg-NGs, HUVEC (human umbilical vein endothelial cell line), HEK-293T (human embryonic kidney 293 cell line), RD (human rhabdomyosarcoma cell line), HepG2 (human liver cancer cell line), and A549 (human lung adenocarcinoma epithelial cell line) cells were used. All cell lines were obtained from American Type Culture Collection (ATCC, Manassas, Va., USA).

HUVEC and A549 cell lines were cultured in M199 and F-12K media, respectively, and HEK-293T, RD, and HepG2 cell lines were cultured in the DMEM medium. The medium was supplemented with fetal bovine serum (FBS, 10%), antibiotic-antimycotic (1%), L-glutamine (2.0 mM), and nonessential amino acids (NEAA, 1%) in 5% $CO_2$ at 37° C. The cell number was determined by the trypan blue exclusion assay (Gibco, Thermo Fisher Scientific, Waltham, Mass., USA), and the cell viability was determined using the PrestoBlue assay. Briefly, approximately $1.0 \times 10^4$ cells per well of all cell lines were separately incubated with the respective culture medium for 12 h at 37° C. containing 5% $CO_2$ in 96-well plates. Then, the culture medium in each well was replaced with 100 μL of medium containing GNS/Alg-NGs (0.1 mg/mL to 1.0 mg/mL), followed by incubation for 72 h. The cells were carefully rinsed thrice with PBS and treated with the PrestoBlue reagent (ten-fold dilution, 100 μL per well) for 4 h. Then, the fluorescence intensities (IF590) were measured at an excitation/emission wavelength of 540/590 nm (Synergy 4 Multi-Mode; BioTek Instruments). Because fluorescence intensity was directly correlated with cell quantity, the cell viability in the control set (media without GNS/Alg-NGs) was assumed to be 100%.

The live/dead viability/cytotoxicity kit (Invitrogen) was further used to examine live and dead cells. The HEK-293T cells were maintained in a cell culture chamber dissolved in the DMEM medium at 37° C. humidified atmosphere containing 95% air and 5% $CO_2$. HEK-293T cell lines were cultured in 24-well plates for 72 h (about $1.0 \times 10^5$ cells/well). Subsequently, the culture solution was replaced with a culture solution containing GNS/Alg-NGs (0.1 mg/mL to 1.0 mg/mL) and cultured for 72 h. The HEK-293T cell cultures, after washing three times with PBS, were stained with a working solution consisting of PBS (1 mL), ethidium homodimer-1 (EthD-1; 2 μL), and calcein acetoxymethyl (calcein-AM; 0.5 μL) and viewed under a fluorescence microscope (Axiovert 200 M, Carl Zeiss, Oberkochen, Germany).

(11) Hemolysis Assays

The human red blood cells (RBCs) for the hemolysis assays were donated from MMH (Taipei, Taiwan). Blood samples were collected from a healthy volunteer (male, 25 years old) into tubes containing ethylenediaminetetraacetic acid (EDTA) and immediately (within 30 min of the collection) centrifuged (relative centrifugal force (RCF) 3,000 g, 10 min, 4° C.) to remove the serum. The RBCs were diluted with sterile isotonic physiological buffer to obtain an RBC stock suspension (about 4.0 vol % blood cells). For the analysis, 100 μL of the RBC stock suspension was incubated with aliquots of GNS/Alg-NGs dispersions (0.1 mg/mL to 1.0 mg/mL) in 1.5 mL vials at 37° C. for 1 h. Then, the aliquots were centrifuged at an RCF of 1,000 g for 10 min Hemolysis was measured based on the absorption of hemoglobin at 576 nm ($OD_{576}$) in the supernatant (200 μL). For the 0% hemolysis reference ($OD_{576}$ blank), a sterile isotonic physiological buffer was used. The positive control expressing 100% hemolysis was prepared by adding ultrapure water to an RBC suspension ($OD_{576}$ ultrapure water). The hemolysis activity was calculated as follows:

Hemolysis (%)=[$OD_{576\ GNS/Alg-NGs}$−$OD_{576\ blank}$)/ ($OD_{576\ ultrapure\ water}$−$OD_{576\ blank}$)]×100%.

Example 1: Synthesis of Graphene-Like Nanosheet (GNS)-Embedded Polyphenolic Alginate Nanogels (GNS/Alg-NGs)

The graphene-like nanosheet-embedded polyphenolic-alginate nanogels (hereinafter referred to as "GNS/Alg-NGs") was synthesized from sodium alginate by heating. Briefly, 50 mg of sodium alginate was placed in a 20 mL glass sample bottle, and dry heated in a laboratory-grade convection oven (DH 300, Dengyng, Taiwan) at 150° C., 180° C., 210° C., 240° C., 270° C., or 300° C. for 3 h. The as-obtained solid product was allowed to cool down and then dissolved in 5.0 mL of deionized water by sonication for 1 h. The larger particles were removed by centrifugation at a relative centrifugation force (RCF) of 500 g for 30 min. The as-obtained GNS/Alg-NGs dispersions were stored at 4° C. for future use.

The alginate nanogels (hereinafter referred to as "Alg-NGs") or GNS/Alg-NGs obtained after dry heating at 150° C., 180° C., 210° C., 240° C., 270° C., or 300° C. were denoted as Alg-NGs-150, Alg-NGs-180, GNS/Alg-NGs-210, GNS/Alg-NGs-240, GNS/Alg-NGs-270, and GNS/Alg-NGs-300, respectively. The product yields range from about 95% to about 36% (as shown in Table 1 below).

Example 2: Characterization of Nanogels

The characterizations of the Alg-NGs or GNS/Alg-NGs dispersions obtained in Example 1 were performed and reported as follows.

(1) Solubility and Viscosity

Figure 2:
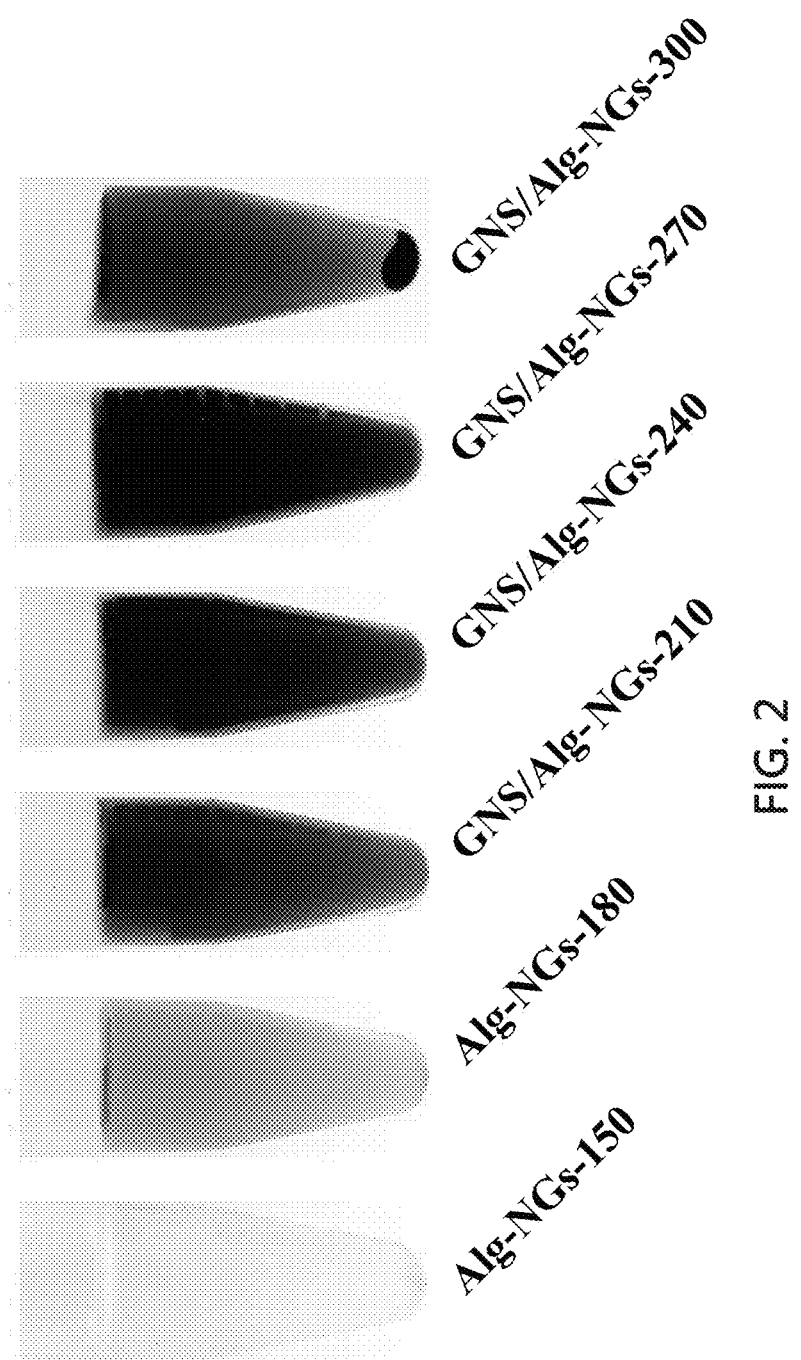
FIG. 2 shows the photographs of the dispersions in deionized water of Alg-NGs-150, Alg-NGs-180, GNS/Alg-NGs-210, GNS/Alg-NGs-240, GNS/Alg-NGs-270, and GNS/Alg-NGs-300 after centrifugation progress.

Firstly, in view of solubility, all of the dispersions except for GNS/Alg-NGs-300 have high solubility in water (>50 mg/mL) at 25° C., as shown in FIG. 2. Further, at 25° C., sodium alginate solution has high viscosity (442.2 mPas, 10 mg/mL), whereas most Alg-NGs and GNS/Alg-NGs have low viscosity even at five times higher concentration (<5.2 mPas, 50 mg/mL). The decreased viscosity of the heated products suggested that the polymeric characteristics of alginate were destroyed after heating.

(2) Hydrodynamic Diameter and Zeta Potential

Referring to Table 1 below, the hydrodynamic diameters of Alg-NGs or GNS/Alg-NGs synthesized at 150° C. to 300° C. showed a decrease from 410.2 nm to 52.0 nm, due to higher decomposition and carbonization with increasing temperature. Further, the hydrodynamic diameter of Alg-NGs-150 (410.2 nm) was only slightly smaller than that of untreated sodium alginate (474.6 nm), indicating that no significant pyrolysis occurred when heated at 150° C. Compared to GNS/Alg-NGs-270, GNS/Alg-NGs-300 exhibited larger hydrodynamic size (198.2 nm), due to over-crosslinking and carbonization.

TABLE 1

Product yield and characteristics of the dispersions prepared from sodium alginate without treatment and after dry heating

| | Product yield (%) | Zeta potential (mV; n = 5) | Hydrodynamic diameter (nm; n = 5) | Fluorescence quantum yield (QY) (%)[a] | Elemental compositions (wt %)[b] | | |
|---|---|---|---|---|---|---|---|
| | | | | | C | H | O |
| Sodium alginate | — | −86.2 ± 2.1 | 474.6 ± 155.7 | <0.01 | 29.98 | 5.02 | 55.33 |
| Alg-NGs-150 | 95.2 | −45.8 ± 1.3 | 410.2 ± 77.9 | <0.01 | 29.38 | 5.20 | 55.63 |
| Alg-NGs-180 | 85.3 | −41.8 ± 2.4 | 327.4 ± 65.3 | 14.30 | 30.74 | 5.00 | 54.61 |
| GNS/Alg-NGs-210 | 60.9 | −40.5 ± 6.9 | 153.1 ± 38.4 | 8.30 | 36.71 | 4.63 | 46.16 |
| GNS/Alg-NGs-240 | 48.3 | −34.2 ± 4.2 | 78.5 ± 25.7 | 4.48 | 34.83 | 4.88 | 45.48 |
| GNS/Alg-NGs-270 | 46.8 | −31.7 ± 5.1 | 52.0 ± 11.3 | 3.22 | 33.53 | 4.81 | 44.57 |
| GNS/Alg-NGs-300 | 36.1 | −30.4 ± 0.8 | 198.2 ± 49.9 | 2.09 | 35.19 | 3.92 | 44.00 |

[a]compared to quinine sulfate (QY: 54% in 0.1M $H_2SO_4$).
[b]determined by elemental analysis.

Next, as shown in Table 1 above, the zeta potential of untreated sodium alginate was about −86 mV, because of its negatively charged carboxylic groups on the C-6 position of the monomeric units. In comparison, the Alg-NGs and GNS/Alg-NGs exhibited zeta potential values of about −46 mV to about −30 mV, as a result of the dehydration, condensation of hydroxyl groups and carboxylic groups, and carbonization.

Figure 3:
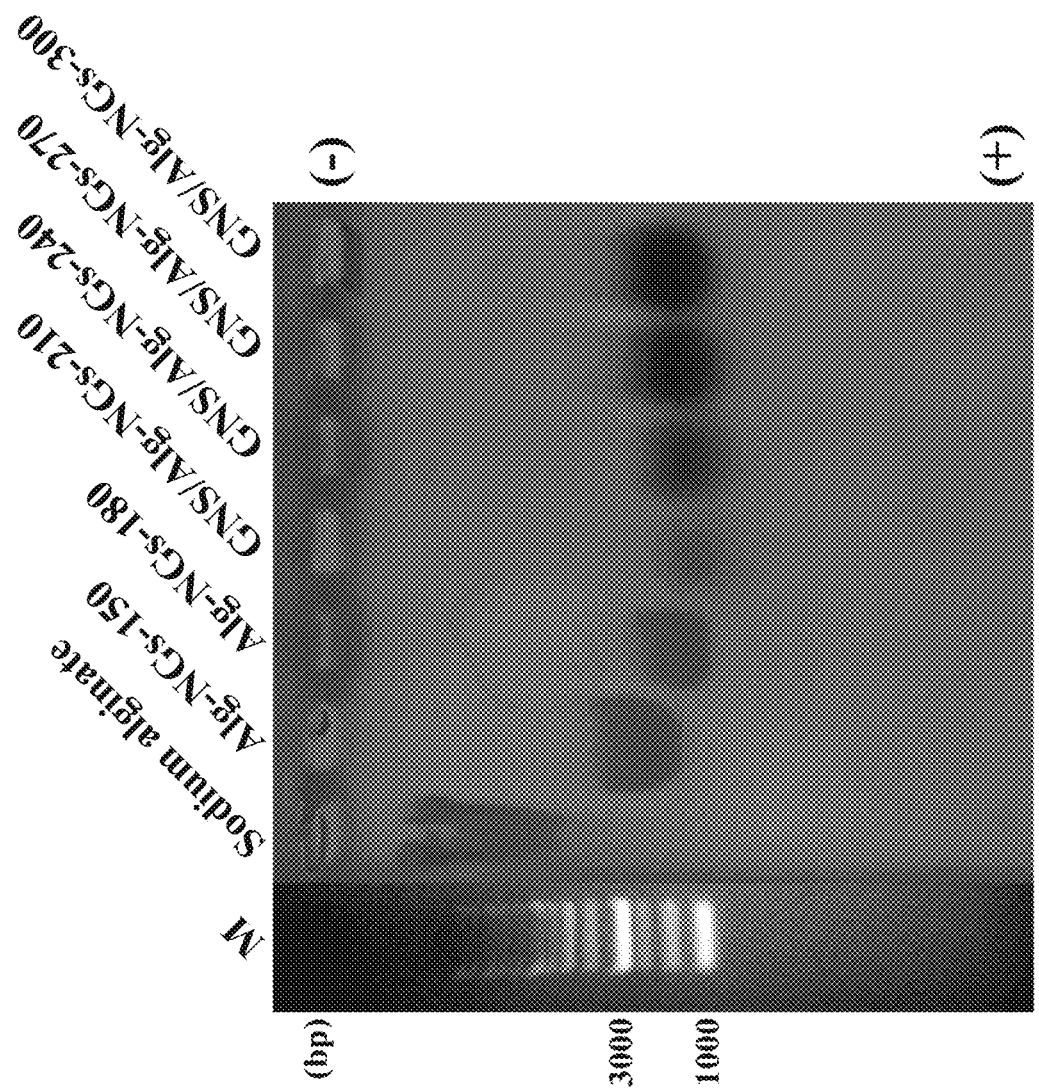
FIG. 3 shows the charge and size distribution of sodium alginate, Alg-NGs, and GNS/Alg-NGs measured by agarose gel electrophoresis assay.

The size distributions of the Alg-NGs and GNS/Alg-NGs were further confirmed by agarose gel electrophoresis assay, and the results were shown in FIG. 3. It was observed that the size distributions of Alg-NGs and GNS/Alg-NGs were in agreement with the hydrodynamic diameters and zeta potential values thereof as disclosed above.

(3) Transmission Electron Microscopy (TEM) Images

Figures 4A, 4B:
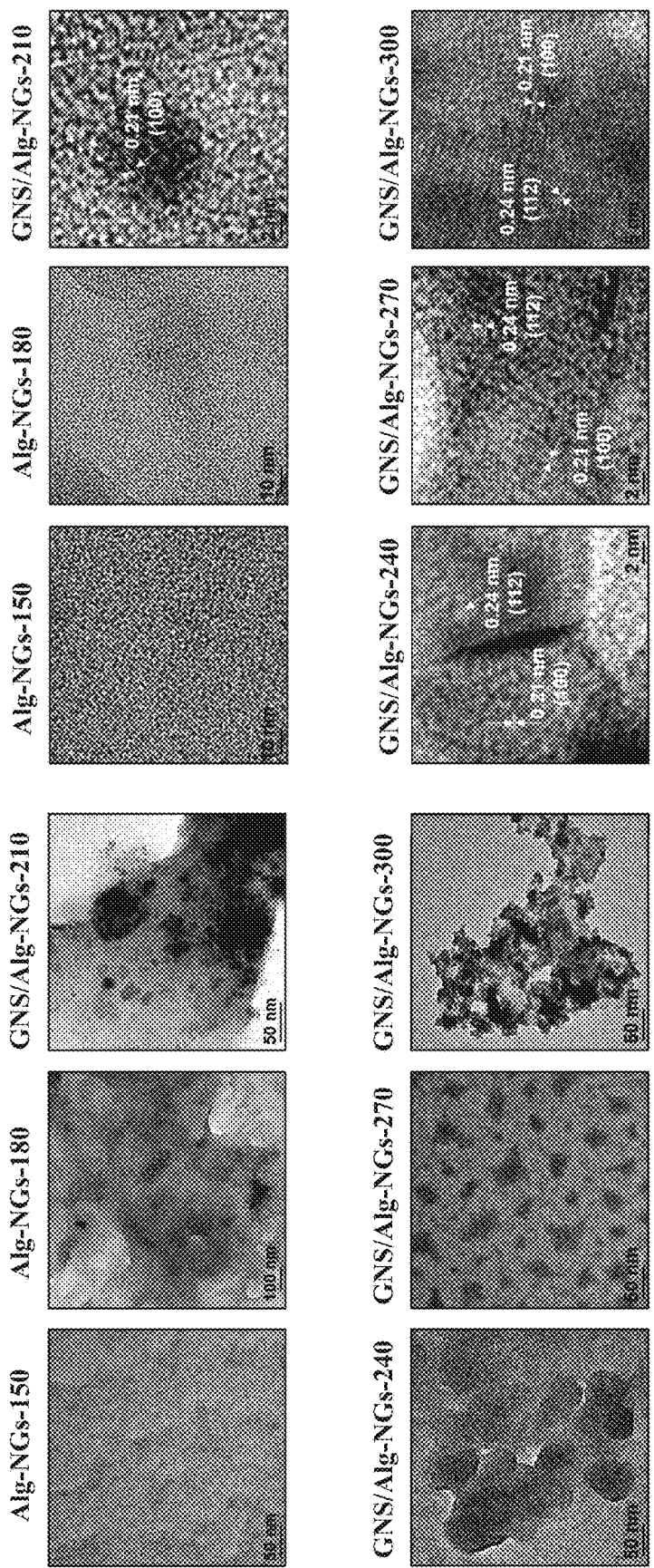
FIGS. 4A and 4B show the transmission electron microscopy (TEM) images and the high-resolution transmission electron microscopy (HRTEM) images of the as-prepared products synthesized at different temperatures, respectively.

By the TEM images shown in FIG. 4A, it was confirmed that Alg-NGs-150 and Alg-NGs-180 contained gel-like crosslinking polymers formed by condensation reactions. In contrast, the GNS/Alg-NGs heated at 210° C. to 300° C. exhibited distinct particles that form along with polymer matrix. It is noted that the TEM image of the GNS/Alg-NGs-270 revealed a particle size with a mean diameter of 48.7±6.5 nm (100 counts). In contrast, relatively low solubility (<0.1 mg/mL) and large-sized carbon particles were observed in GNS/Alg-NGs-300, due to a higher degree of carbonization of sodium alginate.

High-resolution TEM (HRTEM) images shown in FIG. 4B further demonstrated d-spacing values of 0.21 nm and 0.24 nm in the carbonized products, which were attributed to the lattice planes of the (100) and (112) facets of graphene-inter-planar spacing, respectively, and revealed the formation of crystalline graphene-like structures in addition to the cross-linked nanogel matrix. Alg-NGs-150 and Alg-NGs-180 did not show lattice planes in the HRTEM images, however, thereby indicating no formation of a crystalline carbon core formation during heating at low temperatures.

(4) UV-Visible Absorption Spectra

Referring to FIG. 5A, UV-visible absorption spectra showed an absorption band at 280 nm for all Alg-NGs and GNS/Alg-NGs, except for Alg-NGs-150. This band corresponded to the π→π* transitions of conjugated C=C bonds ($sp^2$ clusters), and indicated the formation of graphitic carbon during carbonization of sodium alginate. A shoulder band was observed at 320 nm to 360 nm for Alg-NGs-180 and all of the GNS/Alg-NGs, and ascribed to the n→π* edge transitions of C=O bonds and/or interlayer π→π* charge transfer, supporting the presence of oxygen-containing functional groups on the Alg-NGs-180 and GNS/Alg-NGs. It was further observed that sodium alginate underwent a higher degree of carbonization at 240° C. to 300° C., leading to the formation of a larger graphitic carbon network resulting in strong π→π* transitions of C=C bonds.

Next, the fluorescence spectra were examined Upon excitation with a wavelength of 365 nm, the GNS/Alg-NGs exhibited a broad fluorescence band centered at about 450 nm (FIG. 5B). The strong fluorescence of the Alg-NGs and GNS/Alg-NGs prepared at 150° C. to 210° C. might be due to the as-formed graphene-like nanosheets embedded in the cross-linking polymer matrix of the nanogels (as shown in Table 1 and FIG. 5B). The lower fluorescence intensity of GNS/Alg-NGs prepared at >210° C. was mainly due to the higher degree of carbonization, which was evident from the decreased oxygen content for GNS/Alg-NGs with increasing synthesis temperature (Table 1).

(5) X-Ray Diffraction (XRD) Spectra

Figure 6:
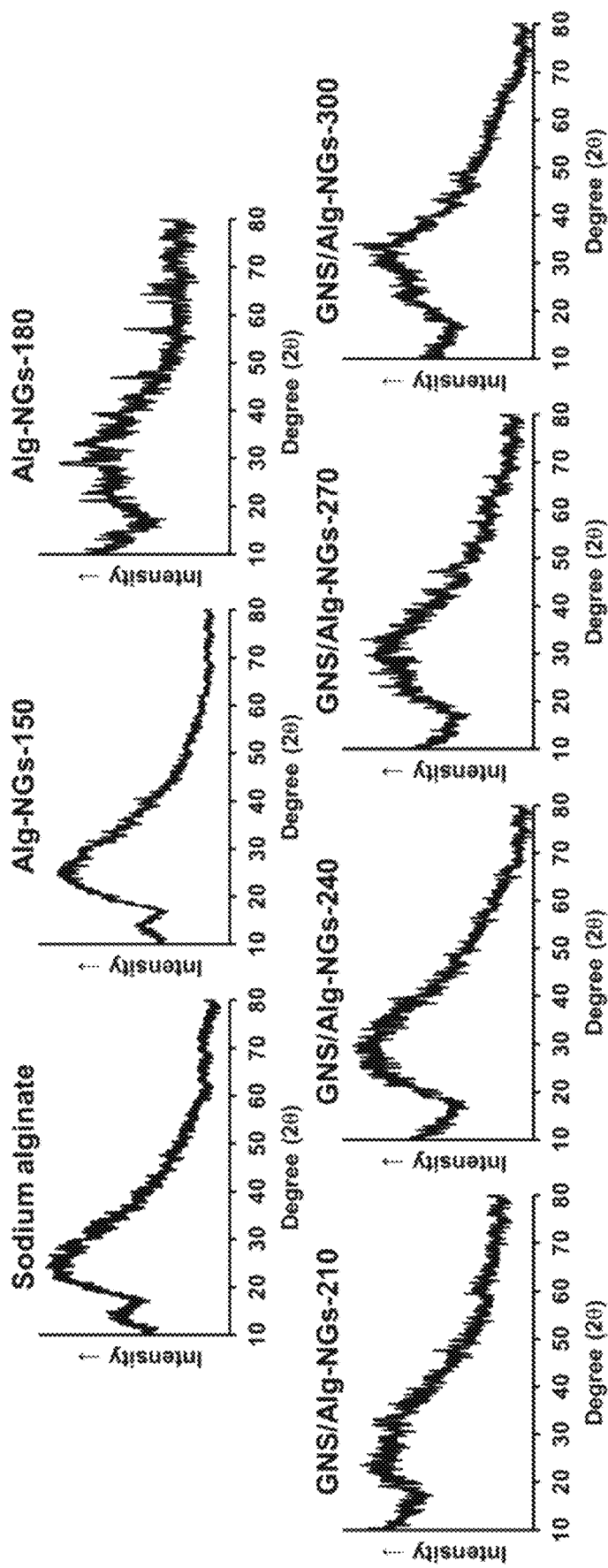
FIG. 6 shows the X-ray diffraction (XRD) spectra of sodium alginate, Alg-NGs, and GNS/Alg-NGs.

As shown in FIG. 6, the XRD spectra of sodium alginate, Alg-NGs, and GNS/Alg-NGs revealed that significant changes occurred in the alignment of crystalline polyguluronate (G form) units of sodium alginate upon heating. While most of the G form characteristics were preserved in the Alg-NGs-150, inter-planar spacing (002) of 0.33 nm corresponding to facets of graphene-like carbon structure appeared at higher temperatures (>210° C.) and the characteristic G form peak disappeared, indicating partial carbonization of sodium alginate.

Figure 7A:
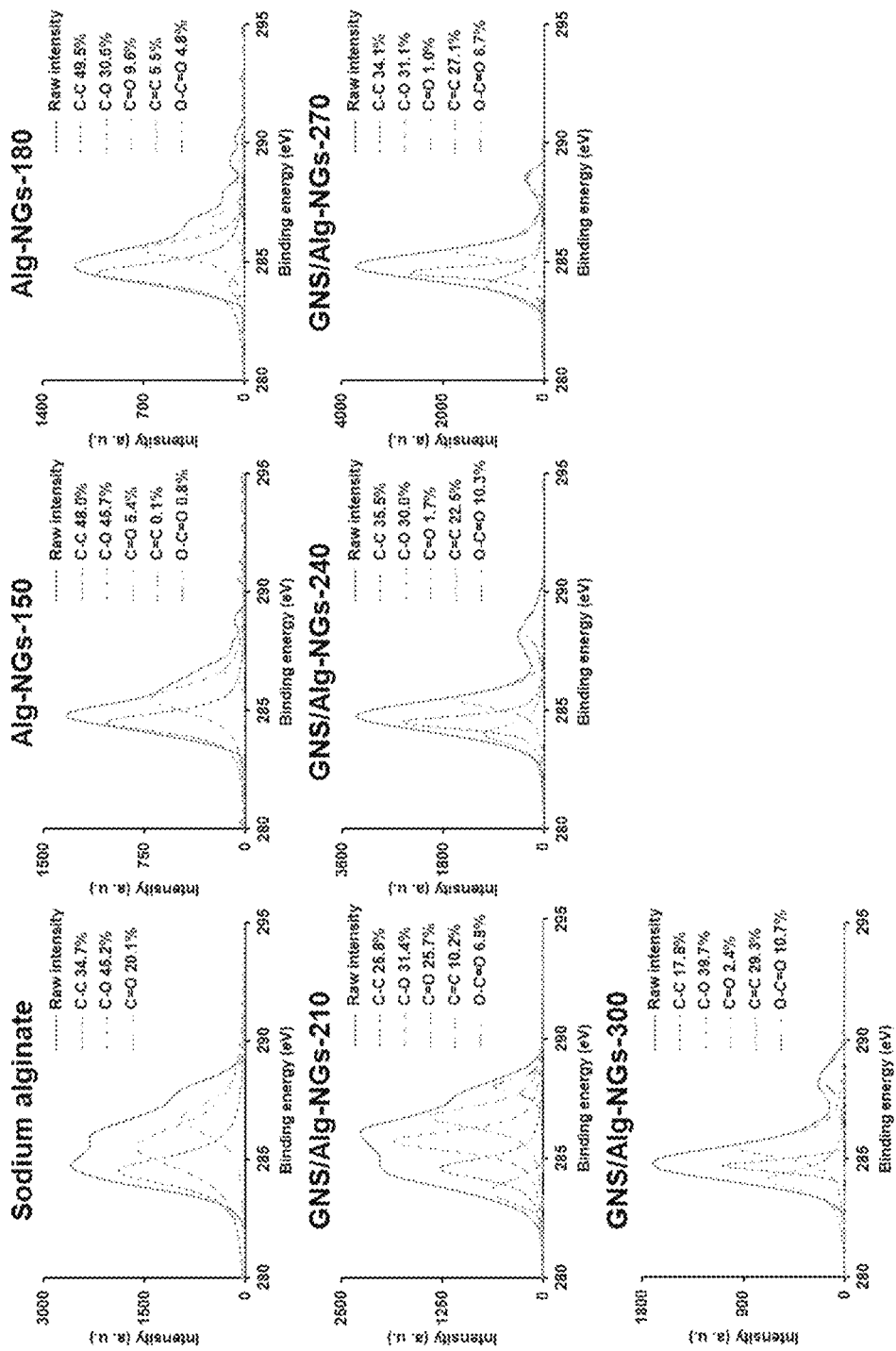
FIGS. 7A and 7B show the C1s XPS spectra and the O1s XPS spectra of sodium alginate, Alg-NGs, and GNS/Alg-NGs detected by X-ray photoelectron spectroscopy (XPS), respectively.
Figure 7B:
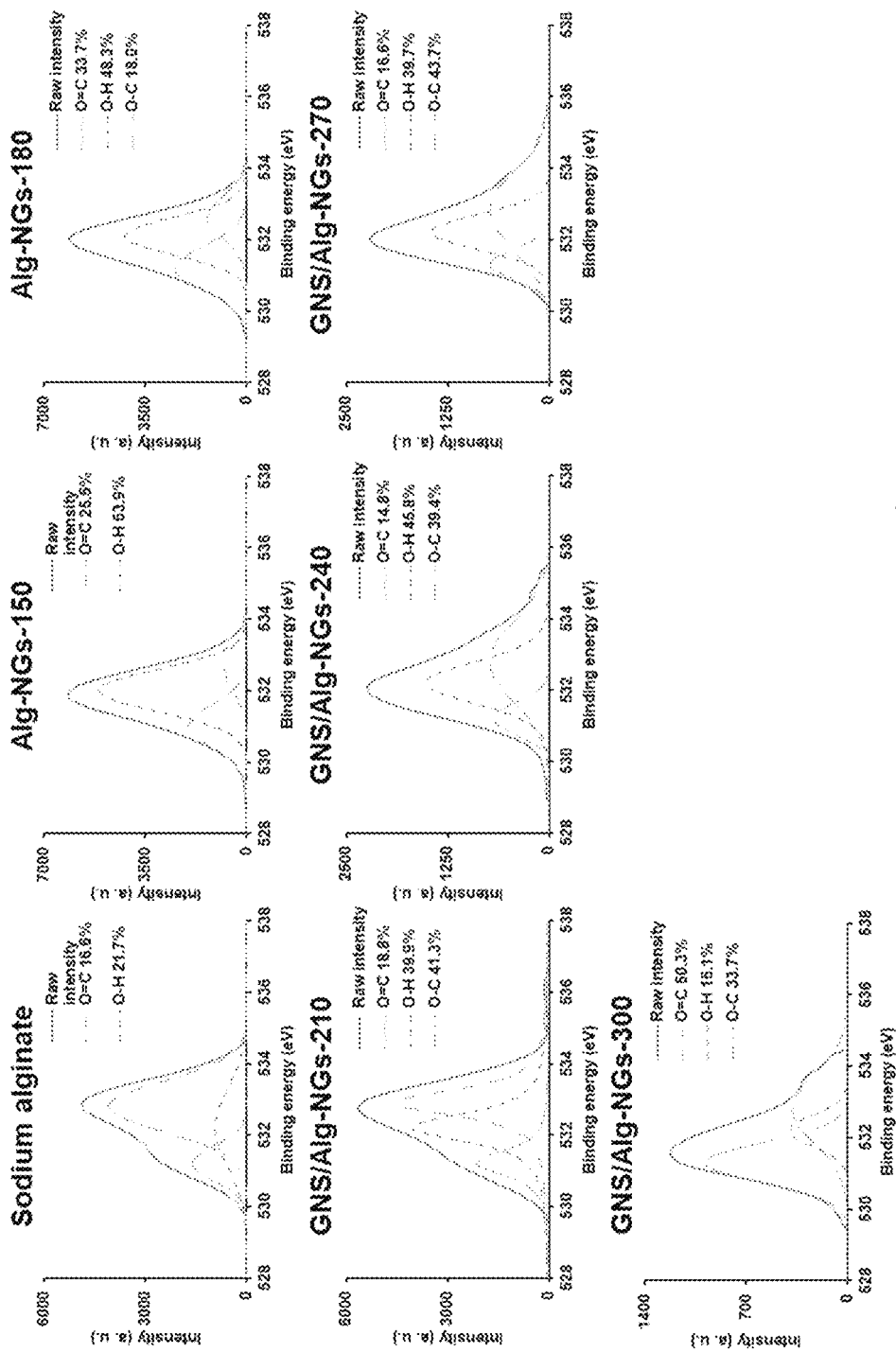

Deconvolution of the C1s spectra obtained by X-ray photoelectron spectroscopy (XPS) of untreated sodium alginate revealed three types of carbon bonds, viz. C—C (284.5 eV; 34.7%), C—O (285.5 eV; 45.2%), and C=O (286.7 eV; 20.1%), as shown in FIG. 7A. For Alg-NGs-150 and Alg-NGs-180, the percentage of C=O bonds decreased to about 5% to 10%, and ester O—C=O (288.5 eV) bonds appeared, due to the condensation reactions. Moreover, the C=C (284.0 eV, about 0.1% to about 29.3%) and O—C=O (about 0.8% to about 10.7%) bonds in Alg-NGs and GNS/Alg-NGs exhibited an increasing trend with synthesis temperatures from 210° C. to 300° C. (FIG. 7A), indicating the formation of the ester bond and sp² carbons in the alginate nanogel structures. Ester bonds were formed through the condensation process between hydroxyl and carboxylic acid groups of the alginate. Similarly, the deconvolution of the O1s XPS spectra of Alg-NGs and GNS/Alg-NGs showed three peaks at 531.2 eV, 532.2 eV, and 532.8 eV, which revealed three types of oxygen bonds, O=C, O—H, and O—C, respectively (FIG. 7B). These results indicated that the Alg-NGs and GNS/Alg-NGs had plenty of hydrophilic groups on their surfaces, such as carboxylic and hydroxyl moieties, which enhanced their aqueous solubility.

(6) Fourier-Transform Infrared Spectroscopy (FT-IR)

Figure 8:
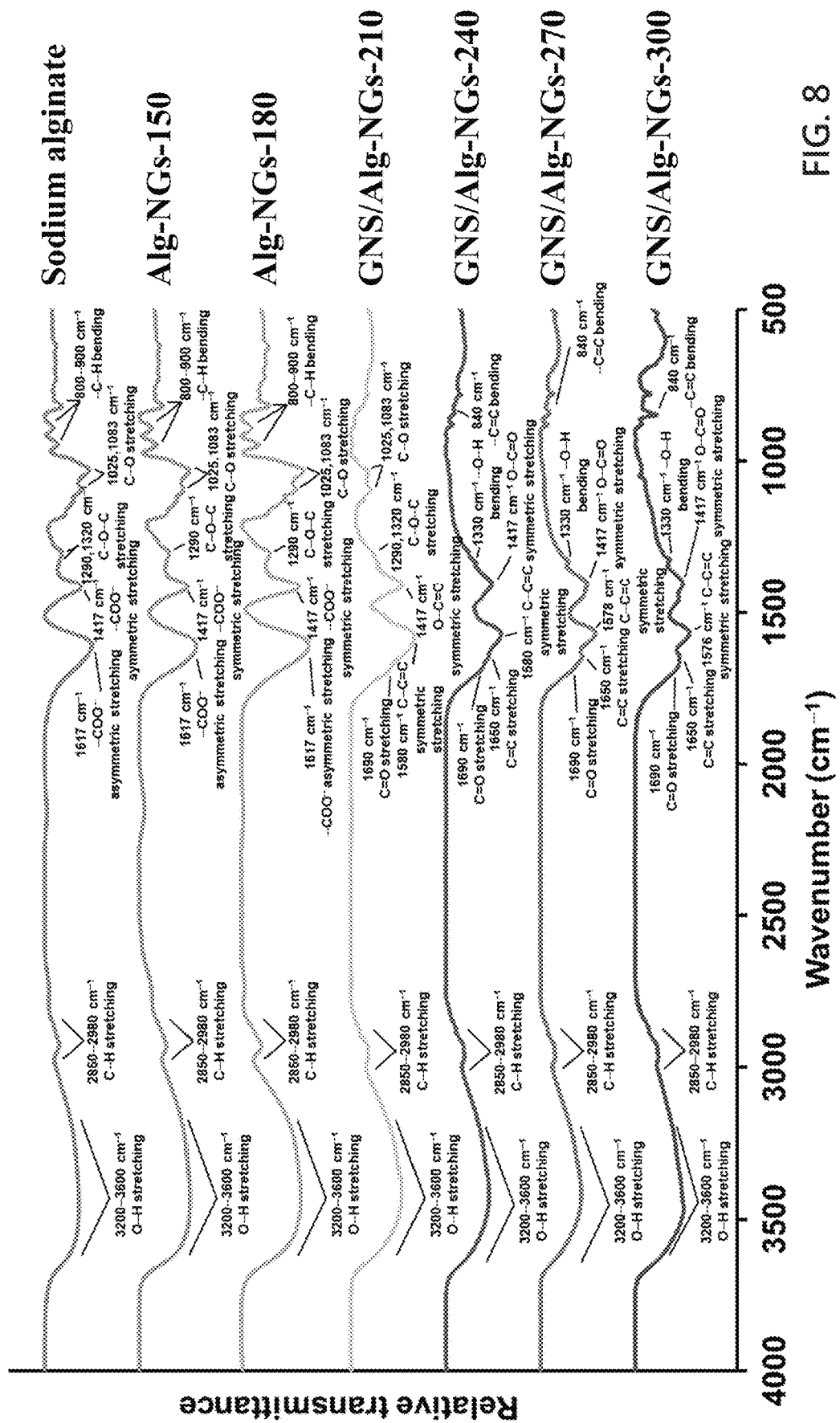
FIG. 8 shows the FT-IR spectra of sodium alginate, Alg-NGs, and GNS/Alg-NGs detected by Fourier transform infrared spectroscopy (FT-IR).

As shown in FIG. 8, the FT-IR spectra showed peaks at 1290 and 1320 $cm^{-1}$, which corresponded to the D-mannuronic (M) and L-guluronic acid (G) moieties of sodium alginate, respectively. The FT-IR spectra of Alg-NGs-150 and Alg-NGs-180 revealed that they had similar chemical structures with that of sodium alginate, due to low carbonization at low temperatures. Upon increasing the synthesis temperature from 210° C. to 300° C., the C—O stretching peak at 1025/1083 $cm^{-1}$ decreased significantly, and a —C=C bending peak at 840 $cm^{-1}$ appeared from 240° C. onwards, thereby indicating the occurrence of carbonization reactions at higher temperatures. Furthermore, the spectrum of GNS/Alg-NGs-270 had a peak at 1330 $cm^{-1}$, which was attributed to the —O—H bending of phenol groups formed by mild aromatization during the carbonization process. Thus, these results suggested that sodium alginate underwent mild carbonization, whereby some functional groups were preserved and new functional groups were formed.

(7) Time Course of the Structure Formation of GNS/Alg-NGs

Figure 9:
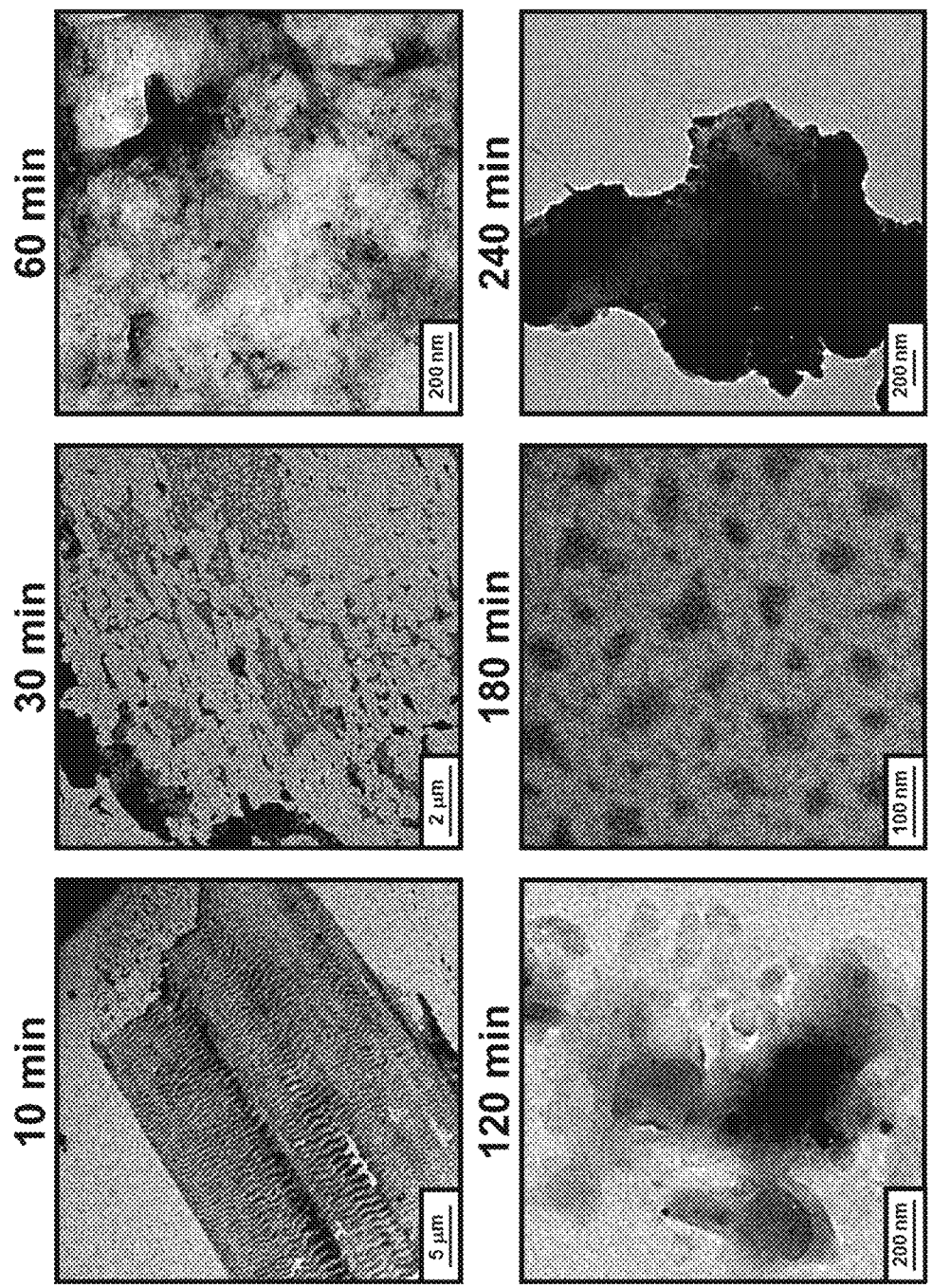
FIG. 9 shows the TEM images of the time-course formation of GNS/Alg-NGs by heating sodium alginate at 270° C. for 10 to 240 min.
Figure 10:
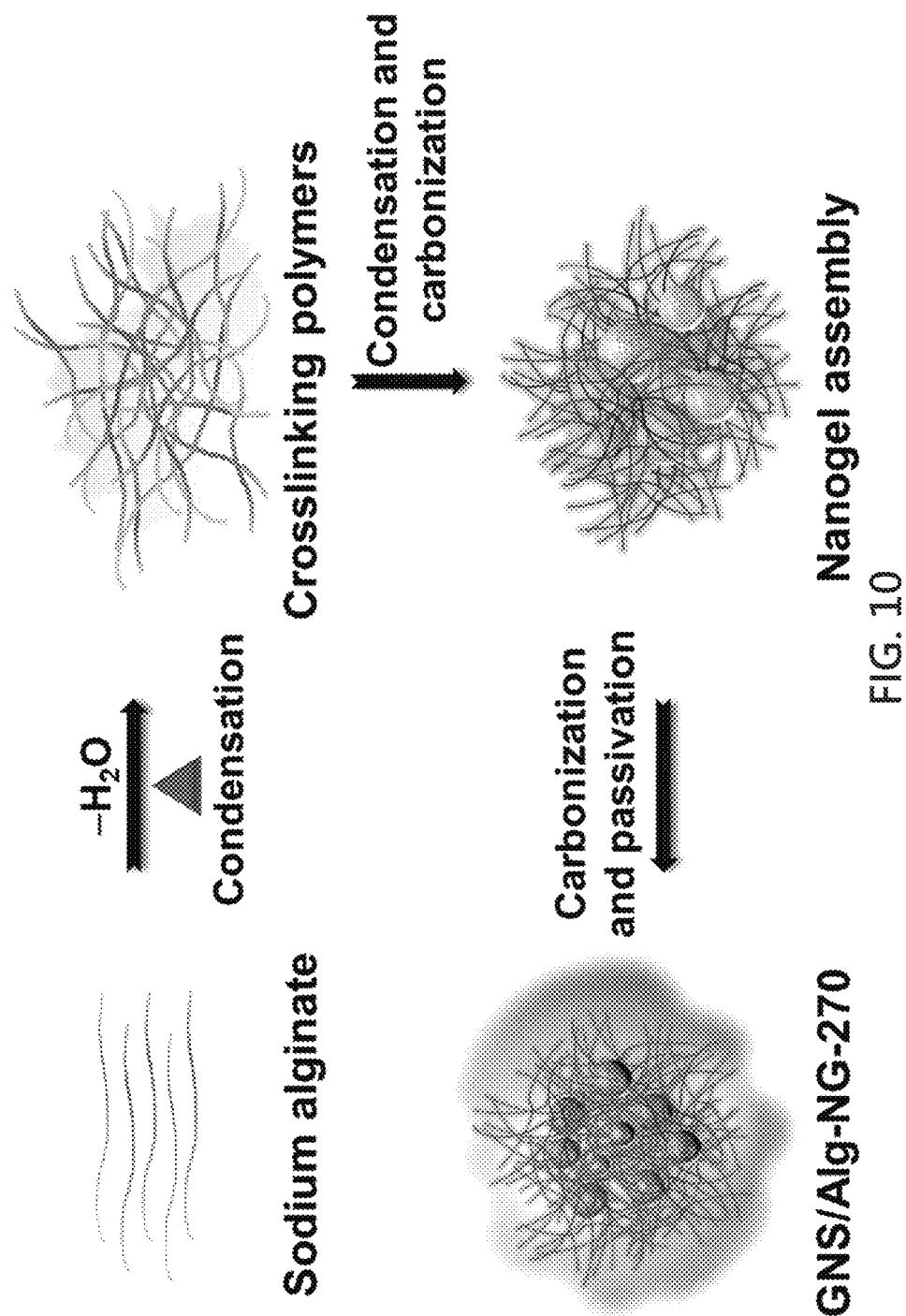
FIG. 10 shows the proposed mechanism of the formation of GNS/Alg-NGs-270.

Time course TEM images of sodium alginate heated at 270° C. showed that a gel-like structure is formed within 10 min heating (FIG. 9). Condensation of the hydroxyl and carboxylic groups of alginate resulted in cross-linking to form supramolecular-like large structures with micrometer sizes. The as-formed supramolecular structures were then fragmented into smaller particles as a result of pyrolysis at the initial stages of carbonization. Further carbonization led to the formation of amorphous carbon clusters upon heating from 30 min to 1 h, whereupon partially carbonized alginate polymeric chains or their fragment molecules constituted the NGs, as illustrated in FIG. 10. In contrast, large carbon residues formed from sodium alginate after heating for 4 h due to a higher degree of carbonization, which resulted in poor aqueous dispersibility. Therefore, a heating time of 3 h was optimal in order to preserve functional groups of sodium alginate and to achieve maximum aqueous dispersibility for bio-applications.

It has been found that, during heating, sodium alginate dehydrates and decomposes to $CO_2$ in three steps: water loss, the formation of a carbonaceous residue, and then $Na_2CO_3$. The thermogravimetric analysis (TGA) of time-course weight loss at constant temperatures (150° C. to 300° C.) for 3 h in the preheated analyzer was consistent with this finding (FIG. 11A). Heating at 150° C. and 180° C. resulted in less than 20% weight loss, due to the loss of water molecules. The weight losses at 210° C., 240° C., 270° C., and 300° C. were about 55% and indicated an increasing trend, suggesting a higher degree of dehydration and thermal decomposition with temperature, despite the melting point of sodium alginate being much higher (>300° C.). Temperature-dependent TGA showed that sodium alginate starts to decompose from 210° C. (FIG. 11B). Under the air atmosphere, dehydration of sodium alginate occurs at about 60° C. to about 210° C., and decomposition at about 210° C. to about 230° C. The differential scanning calorimetry (DSC) curve of the sodium alginate showed a broad endothermic band at 70° C. to 125° C. (FIG. 11C), which was attributed to water loss and the formation of cross-linking polymers by a condensation reaction. The exothermic peak at 240° C. might be a result of the initial stage of decomposition, followed by slight oxidation of carbon atoms, as well as carbonization processes leading to the formation of embedded carbon nanosheets. Some polymer-like alginate and/or its fragment polymers remained on the surfaces of the as-formed GNS/Alg-NGs, thereby conferring specific functional properties and bioactivity.

Example 3: Formation of the Phenolic Polysaccharide

Figure 12:
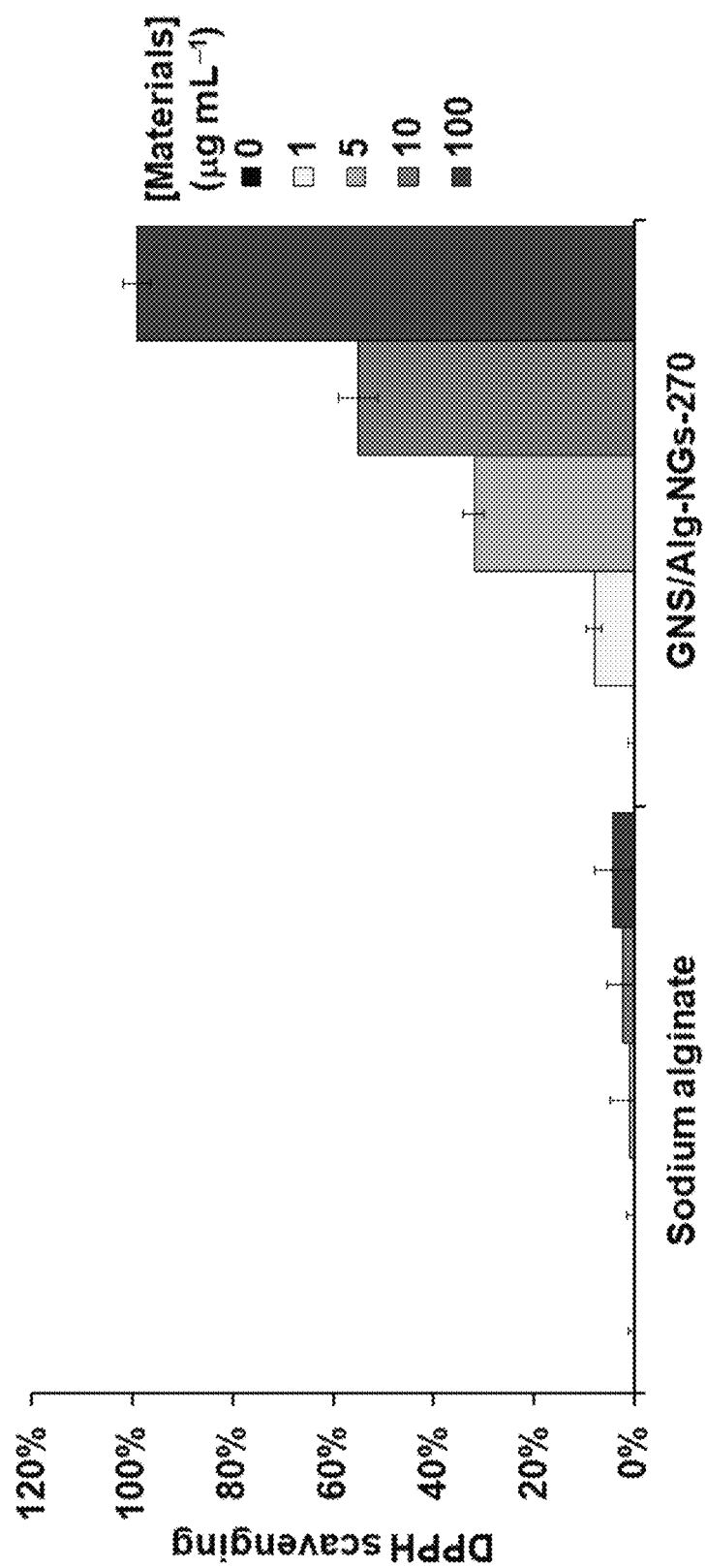
FIG. 12 shows the 2,2-diphenyl-1-picrylhydrazyl (DPPH) scavenging activity of sodium alginate and GNS/Alg-NGs-270.

It was observed that the GNS/Alg-NGs-270 showed an obvious FT-IR peak at 1330 $cm^{-1}$ (FIG. 8), assigned to the phenol group, which had potent antioxidant and anticoagulation activities. To further characterize the presence of polyphenolic functional groups in the GNS/Alg-NGs, the 2,2-diphenyl-1-picrylhydrazyl (DPPH) assay, Folin-Ciocalteu assay, cyclic voltammetry (CV), and nuclear magnetic resonance (NMR) spectroscopy were conducted. The DPPH assay revealed that GNS/Alg-NGs-270 (100 µg/mL) had a superior free radical scavenging ability, about 35-fold higher than that of free sodium alginate, as shown in FIG. 12, and was supportive of the presence of polyphenolic structures. Additionally, the graphene-like nanosheet structures facilitated fast electron transfer and promoted redox reactions on the surface of GNS/Alg-NGs-270.

Next, the total amount of phenols in the GNS/Alg-NGs-270 was quantified by the Folin-Ciocalteu reagent, a mixture of phosphomolybdate and phosphotungstate, so as to evaluate their antioxidant activities. The determined reducing ability of the GNS/Alg-NGs-270 (100 µg/mL) was equivalent to 6.1 µg/mL quercetin (n=5), indicating the formation of phenolic polysaccharides. Conversely, sodium alginate (100 µg/mL) exhibited insignificant reducing ability in Folin-Ciocalteu assay. The cyclic voltammetry of GNS/Alg-NGs-270 in phosphate-buffered saline (PBS) on a glassy carbon electrode (GCE) surface further showed an oxidation peak at 0.8 V, which was consistent with the reports on oxidation of phenol groups.

Figure 13A:
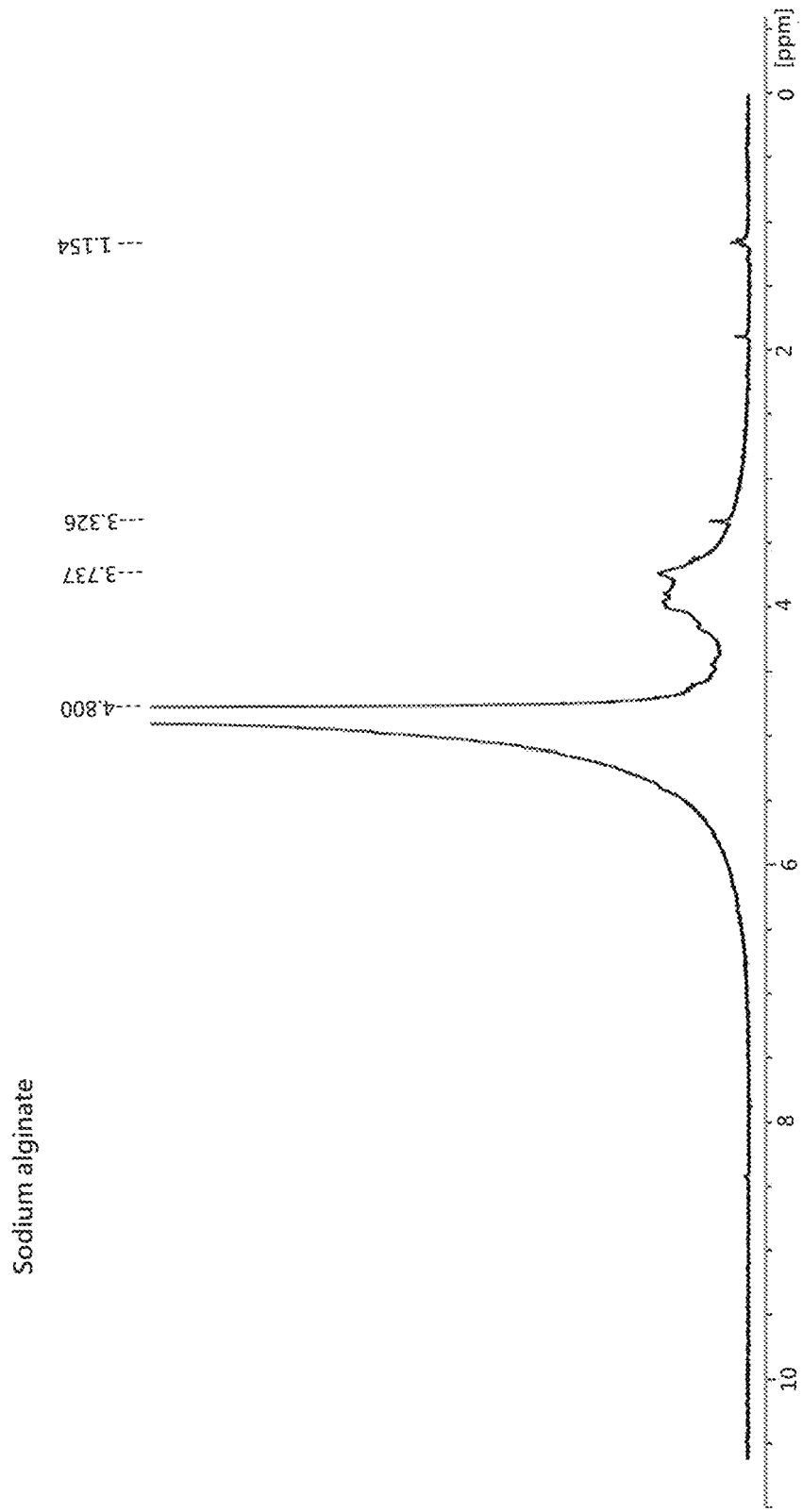
Figure 13C:
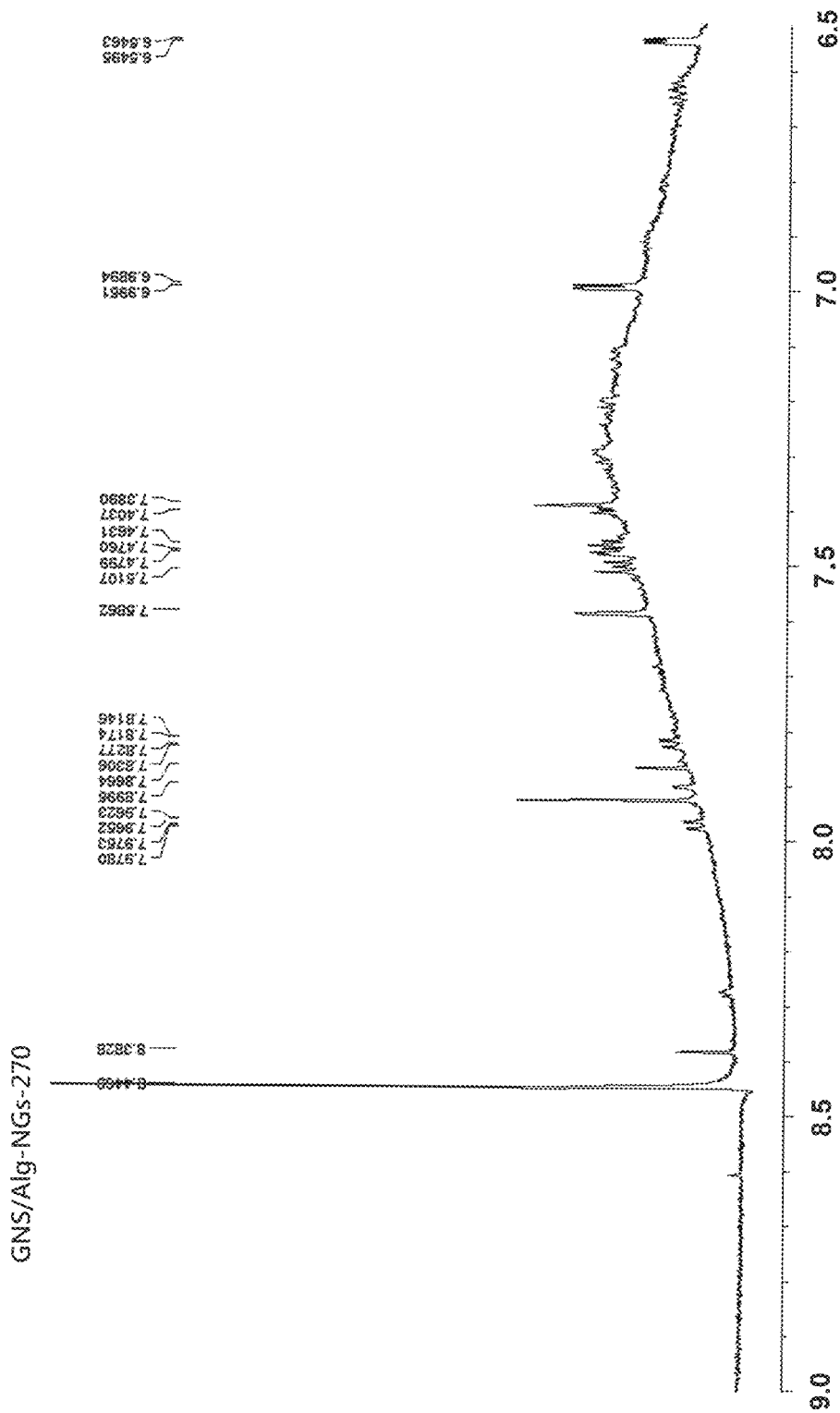

High-resolution $^1$H-NMR spectroscopy was then used for the confirmation of phenolic groups in complicated samples, such as the complex mixture of polyphenol molecules. GNS/Alg-NGs-270 in deuterated water ($D_2O$) showed $sp^3$ C—H protons at 1.0 ppm to 3.0 ppm. There were also a sharp band at 8.4 ppm and broadband with multiple peaks at 6.5 ppm to 9.0 ppm, suggesting the phenol groups on GNS/Alg-NGs-270 engaged in proton exchange between inter-/intra-molecular —OH and —OH and —COOH groups at 298 K (FIGS. 13A to 13C). The FT-IR spectrum and $^1$H NMR spectroscopy of GNS/Alg-NGs-270 showed the formation of phenol groups from the dry heating process of sodium alginate (polysaccharides).

Example 4: Anticoagulation and Antioxidant Activities of GNS/Alg-NGs

The anticoagulation activities of sodium alginate, Alg-NGs and GNS/Alg-NGs were tested by the thrombin clotting time (TCT) assays. As shown in FIGS. 14A and 14B, sodium alginate exhibited negligible anticoagulation activity, whereas GNS/Alg-NGs-270 showed the strongest. The TCT delay time [$(t-t_0)/t_0$, where $t_0$ and t were the time in the absence and presence of inhibitors, respectively] of Alg-NGs-150, Alg-NGs-180, GNS/Alg-NGs-210, GNS/Alg-NGs-240, GNS/Alg-NGs-270, and GNS/Alg-NGs-300 were about 8.7-, about 8.0-, about 37.7-, about 208.7-, about 526.2-, and about 152.7-fold, respectively, longer than that of sodium alginate.

Prothrombin time (PT) and activated partial thromboplastin time (aPTT) assays were further conducted to evaluate the anticoagulation efficacy of Alg-NGs and GNS/Alg-NGs in human plasma samples (FIGS. 14C and 14D). The PT assay was used to evaluate the anticoagulants in the extrinsic coagulation pathway as well as the common pathway in the inhibition of prothrombin, and coagulation factors V, VII, and X. The aPTT assay was used to evaluate the activity of fibrinogen and coagulation factors VIII, IX, XI, XII, II, V, and X. Among the tested materials, the prolonged PT/aPTT values [$(t-t_0)/t_0$, where $t_0$ and t were the PT or aPTT in the absence and presence of inhibitors, respectively] of Alg-NGs-150, Alg-NGs-180, GNS/Alg-NGs-210, GNS/Alg-NGs-240, GNS/Alg-NGs-270, and GNS/Alg-NGs-300 were about 1.0/7.1-, about 2.0/11.4-, about 23.0/41.1-, about 355.0/147.7-, about 777.0/163.6- and about 200.0/118.9-fold, respectively, higher than that of untreated sodium alginate. Thus, the PT and aPTT results revealed the superior anticoagulation properties of GNS/Alg-NGs-270, because of their interaction with several coagulation factors in addition to thrombin.

Figure 15:
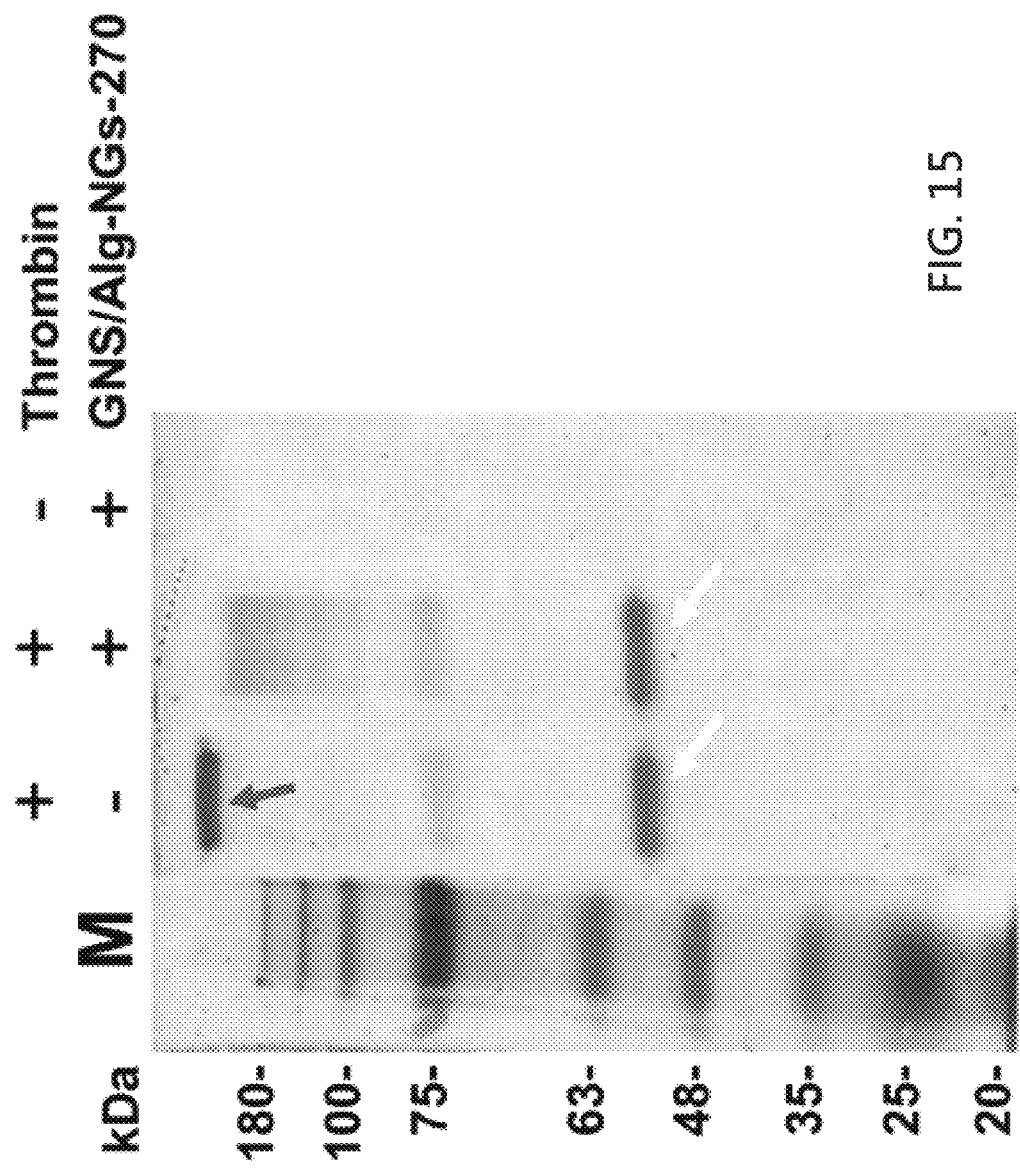
FIG. 15 shows the results of native polyacrylamide gel electrophoresis (native-PAGE) of thrombin with or without GNS/Alg-NGs-270. M: protein ladder marker.
Figure 16:
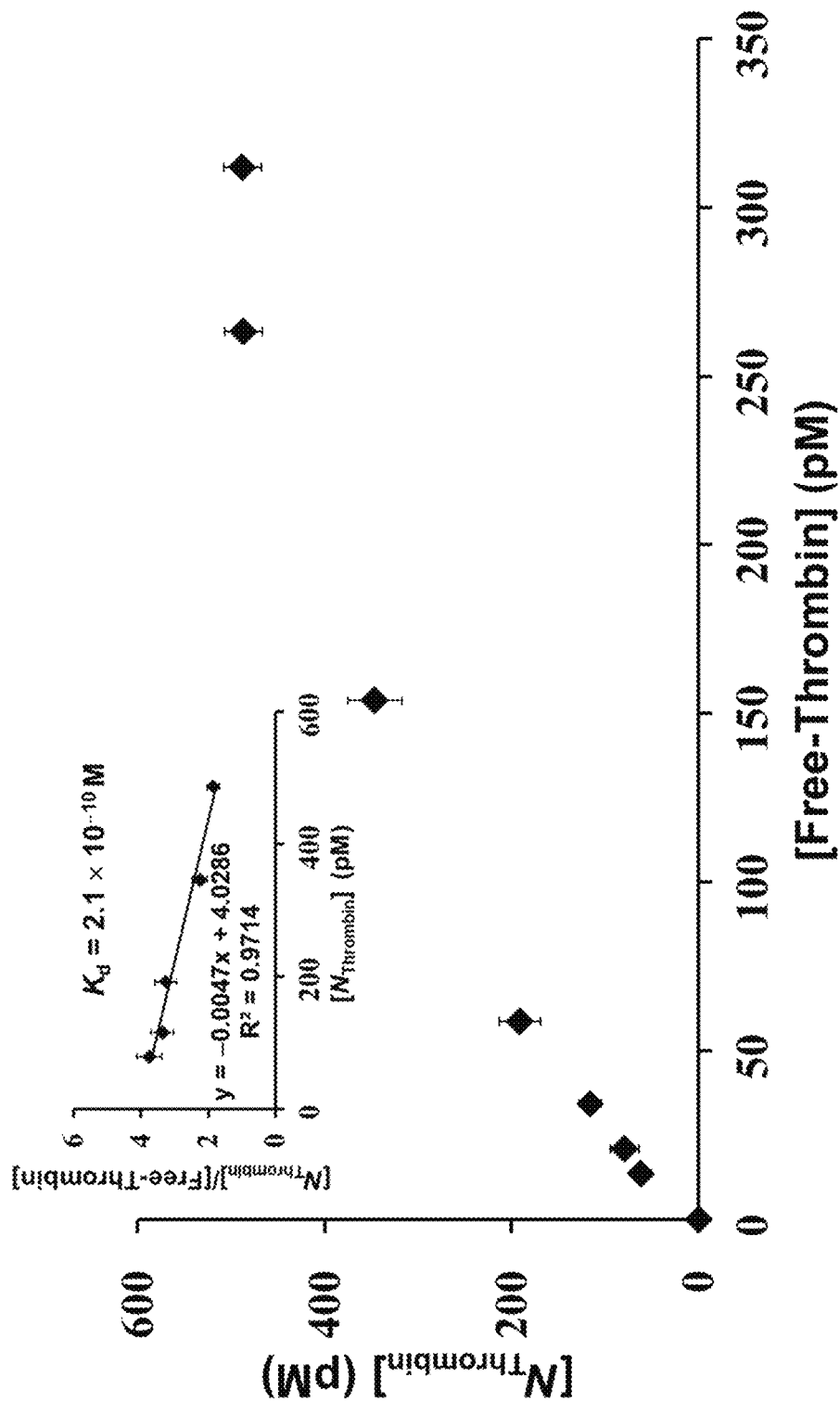
FIG. 16 shows the plot for calculation of the dissociation constants ($K_d$) of thrombin and GNS/Alg-NGs-270.

Further, the interaction between GNS/Alg-NGs-270 and thrombin was verified by native polyacrylamide gel electrophoresis (PAGE), and the results were shown in FIG. 15. It was found that the thrombin band shifted markedly in the presence of GNS/Alg-NGs-270 due to their strong binding. Indeed, negatively charged phenolic/phenolic acid and ester groups that formed on GNS/Alg-NGs-270 during controlled carbonization mediated their strong synergistic interaction with thrombin [dissociation constant ($K_d$)=$2.1 \times 10^{-10}$ M (FIG. 16), and consequently, an extremely high inhibitory potency. In comparison, the $K_d$ with thrombin of the common anticoagulant, heparin, was $1.0 \times 10^{-7}$ M; about 200-fold lower affinity than that of GNS/Alg-NGs-270 with thrombin.

Figure 17:
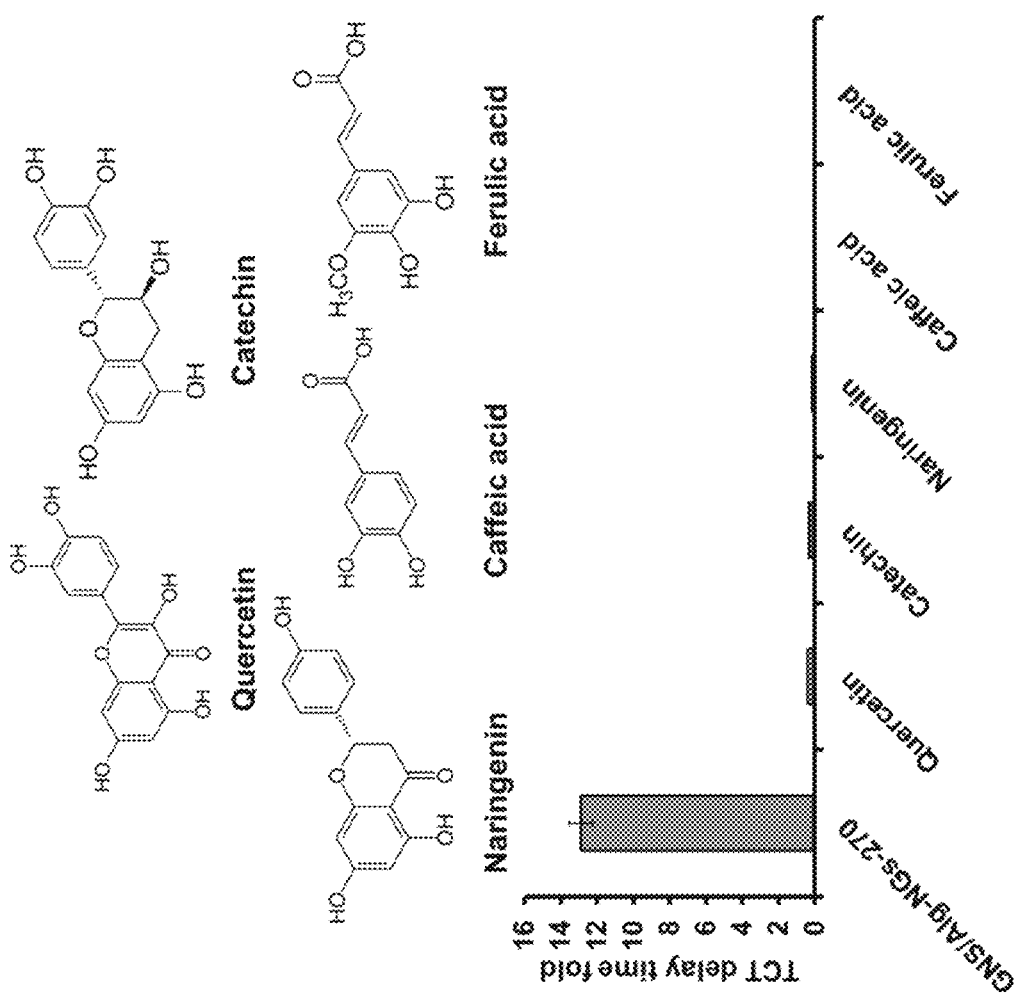
FIG. 17 shows the comparison of thrombin inhibitory activity of polyphenolic GNS/Alg-NGs-270 and natural (poly)phenolic compounds, i.e., quercetin, catechin, naringenin, caffeic acid, and ferulic acid.

To confirm the anticoagulant activity of other polysaccharides, cellulose, agar, dextran, and sulfated polysaccharides, such as κ-carrageenan, fucoidan from *Laminaria japonica*, and chondroitin sulfate sodium salt were tested by the TCT assay after dry heating at 270° C. None of these, however, showed significant anticoagulant activity at a concentration of 1.0 mg/mL (data not shown). In addition, the thrombin inhibitory activity of polyphenolic GNS/Alg-NGs-270 versus natural (poly)phenolic compounds, such as quercetin, catechin, naringenin, caffeic acid, and ferulic acid were further compared by the TCT assay. As shown in FIG. 17, GNS/Alg-NGs-270 displayed about 13-fold longer TCT delay compared to the tested phenol and phenolic acid compounds at a concentration of 0.5 mg/mL.

From the above, the GNS/Alg-NGs-270 exhibited stronger inhibitory activity toward thrombin compared to other NGs, which might be ascribed to its higher content of phenolic or phenolic acid groups. Also, the results from DPPH and Folin-Ciocalteu assays showed that GNS/Alg-NGs-240 and GNS/Alg-NGs-270 possessed stronger antioxidant ability than other NGs, supporting that more polyphenolic and phenolic acid structures formed during the heating of sodium alginate at 270° C. (FIGS. 18A and 18B). The poly-phenolic and poly-carboxylic groups on the NGs facilitated multivalent phenolic acid-like interaction with thrombin, which mediated their strong inhibitory ability.

Figure 19:
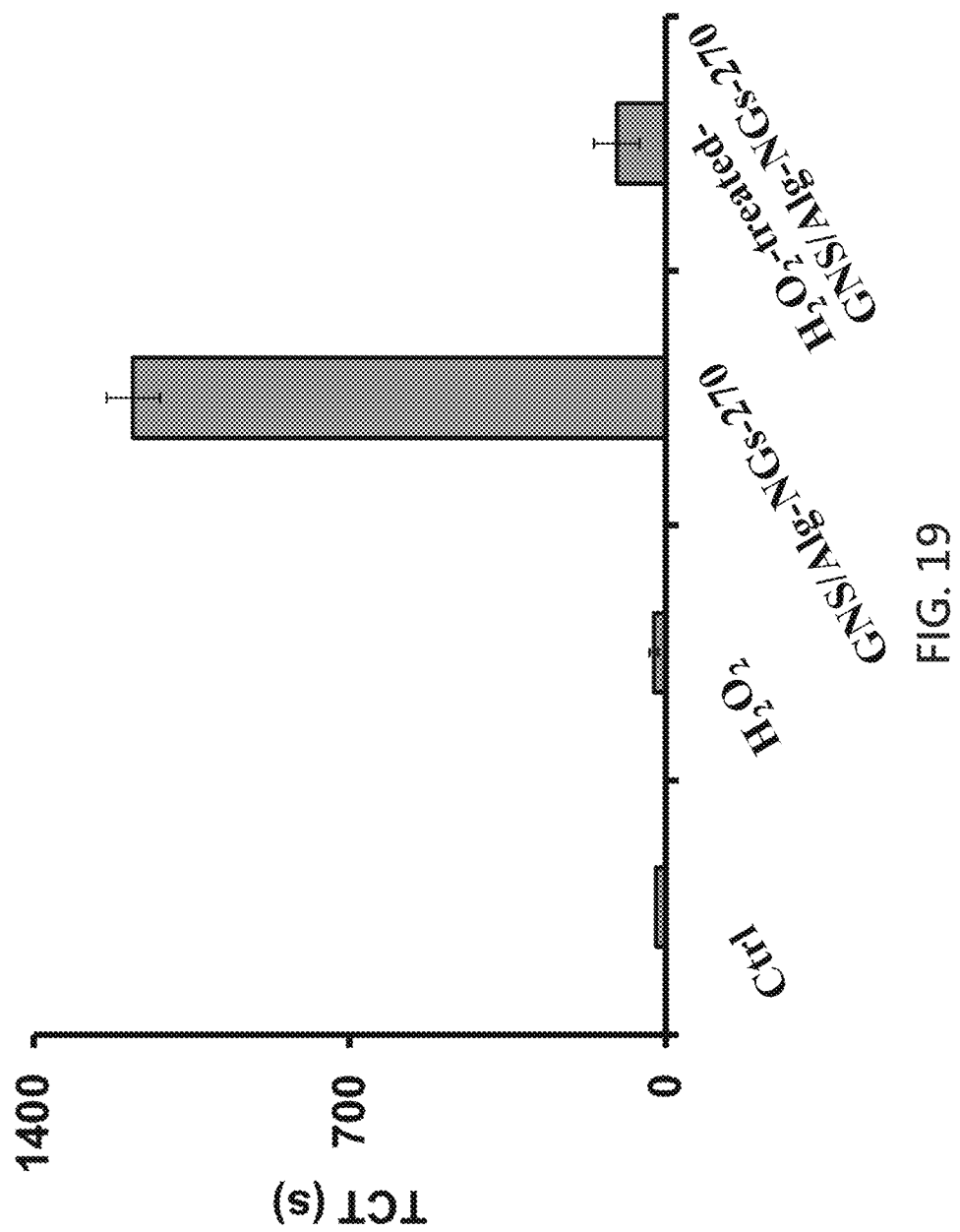
FIG. 19 shows the results of TCT assay of GNS/Alg-NGs-270 after treatment with $H_2O_2$. Ctrl: control.

To further confirm whether the dominant anticoagulation activity toward thrombin is driven by the phenolic group, hydrogen peroxide ($H_2O_2$) was used as an oxidant to eliminate the phenol group of GNS/Alg-NGs-270. It was found that $H_2O_2$ treatment significantly decreased the anticoagulant activity of GNS/Alg-NGs-270 (FIG. 19). In agreement with this, the DPPH scavenging activity of $H_2O_2$-treated GNS/Alg-NGs-270 declined to 20% (data not shown), supporting that $H_2O_2$ treatment oxidized the phenolic groups. Furthermore, as to the products prepared from sodium alginate at 150° C. to 300° C. for 3 h by hydrothermal synthesis, a common method to prepare functional carbon nanomaterials derived from a variety of precursors, none of these showed significant anticoagulation properties at 1.0 mg/mL (data not shown). Therefore, it was found that the dry heating carbonized sodium alginate to form specific polyphenol-like structures, which involved in the anticoagulation property.

Figure 20:
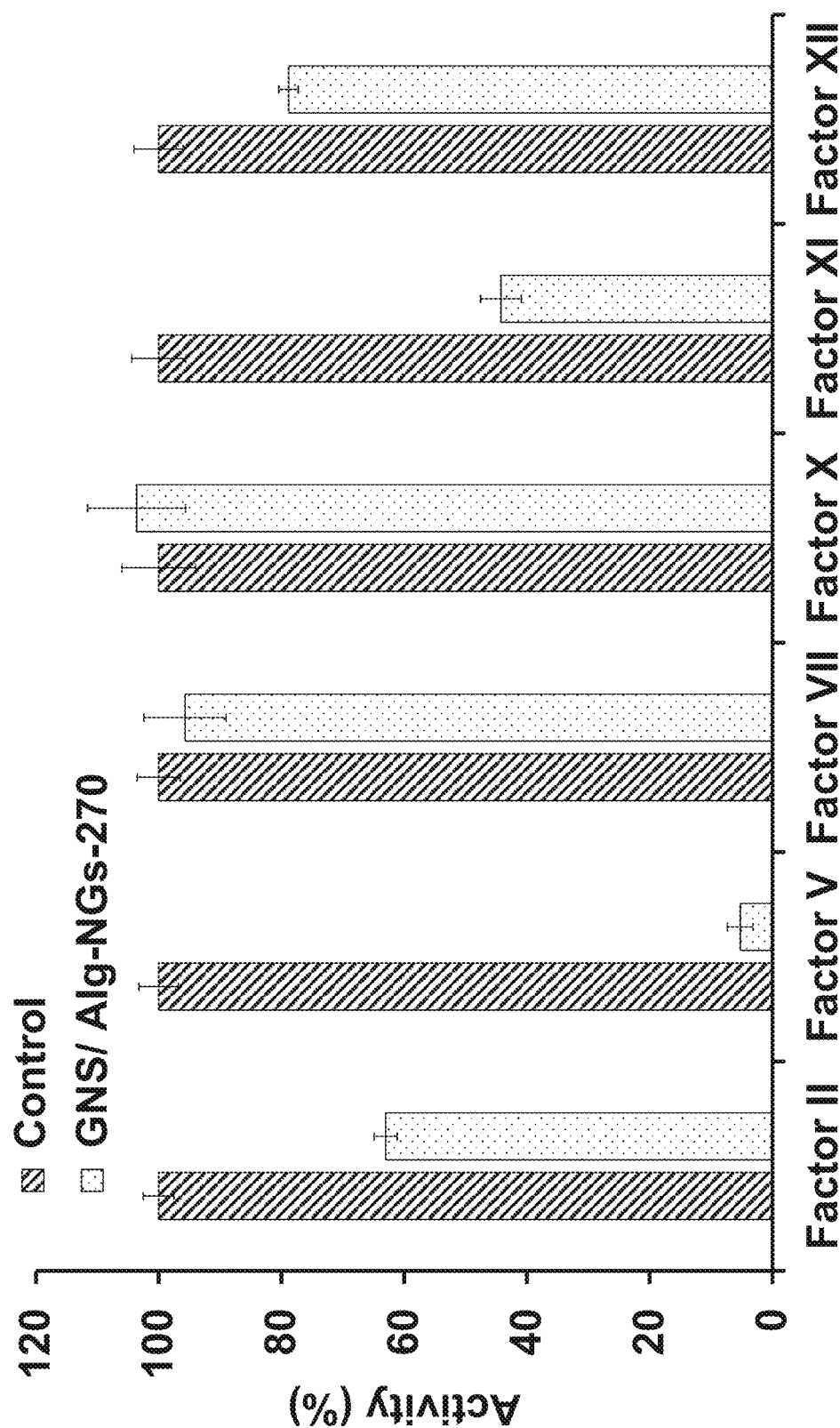
FIG. 20 shows the relative activity of the indicated coagulation factors in the absence (control) or presence of GNS/Alg-NGs-270 in human plasma.

Additionally, to further understand which coagulation factors are involved in the anticoagulation effect of GNS/Alg-NGs-270, the inhibitory activity against factors II, V, VII, X, XI, and XII was examined It was found that factors II, V, XI, and XII were inhibited by GNS/Alg-NGs-270 at a concentration of 2.0 mg/mL (FIG. 20). The coagulation factor II, activated by factor Xa, underwent proteolytic cleavage during the clotting process to form thrombin, which might explain why GNS/Alg-NGs-270 exhibited similar inhibition of factor II. Factors V and VII were related to the PT pathway, and factors XI and XII were related to the aPTT route. Overall, these results indicated that GNS/Alg-NGs-270 inhibited thrombin and other coagulation factors in different pathways, thereby contributing to the suppression of different coagulation pathways.

The anticoagulant activity of GNS/Alg-NGs-270 in human whole blood was further determined by thromboelastography (TEG). The TEG of whole blood samples was recorded after treatment with GNS/Alg-NGs-270, sodium alginate, fucoidan, and other well-known commercial anticoagulants, and thrombin or kaolin were used as an activator.

The anticoagulation efficiency was determined by monitoring blood clot formation. Various parameters could be determined by TEG, including the lag time of initial clot formation (R time), the elapsed time from the beginning of clot formation to a strength amplitude of 20 mm (K time), rate of clot formation (α angle), and maximum amplitude of the mechanical strength of the clot (MA).

Figures 21A, 21B:
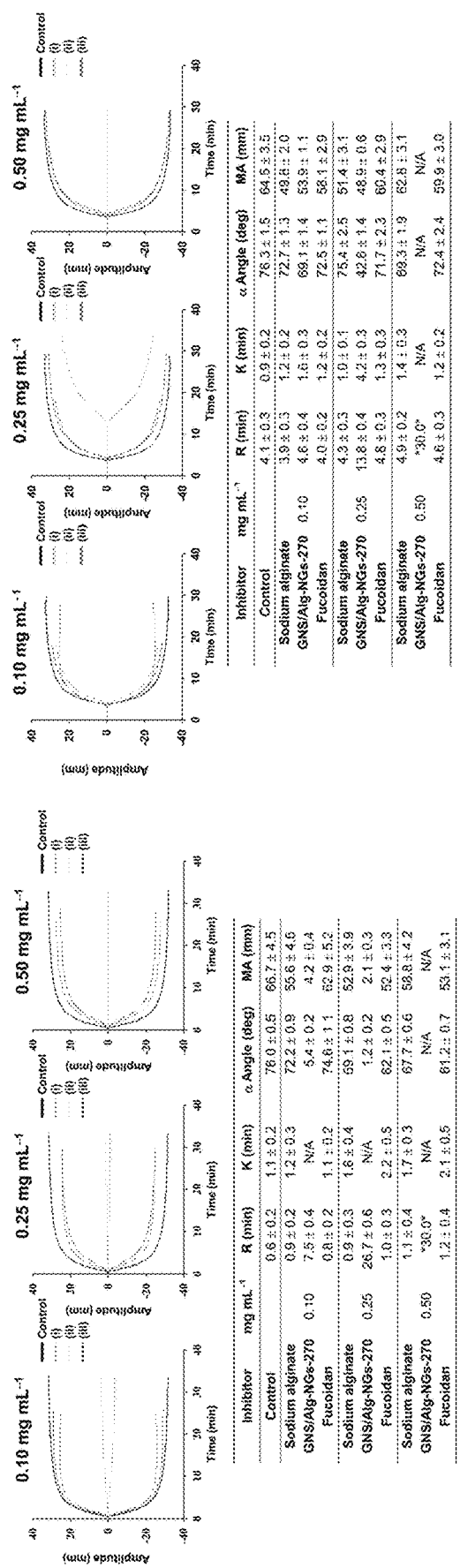
FIGS. 21A and 21B show the anticoagulation effects of sodium alginate (i), GNS/Alg-NGs-270 (ii), and fucoidan (iii) on the thrombin-activated and kaolin-activated thromboelastography (TEG), respectively.

The dose-dependent (0.10 to 0.50 mg/mL) response of sodium alginate, GNS/Alg-NGs-270, and fucoidan on thrombin activated TEG were shown in FIG. 21A. GNS/Alg-NGs-270 resulted in the largest R time, meaning the longest clot formation time. The clot formed in the presence of GNS/Alg-NGs-270 was smaller than 20 mm, and hence the K value was not determined. GNS/Alg-NGs-270 also resulted in the smallest α angle and MA values when compared with sodium alginate and fucoidan, indicating the lowest clot formation rate and clot strength. Furthermore, the dose-dependent anticoagulation on kaolin-activated TEG was also recorded (FIG. 21B). It was observed that GNS/Alg-NGs-270 had the largest R time and K value compared to sodium alginate and fucoidan (FIG. 21B). Moreover, the α angle and MA values showed a similar trend to that of thrombin-activated results.

Example 5: Cytotoxicity and Biocompatibility of GNS/Alg-NGs

GNS/Alg-NGs-270 displayed good anticoagulation and antioxidant activities, as confirmed by the above TCT, aPTT, PT, TEG, DPPH, and Folin-ciocalteu assays. In this example, the cytotoxicity and biocompatibility were further determined.

The cell cytotoxic and hemolytic effects of GNS/Alg-NGs-270 toward five mammalian cell lines and red blood cells (RBCs) were evaluated in vitro. Specifically, the cytotoxicity of GNS/Alg-NGs-270 toward different mammalian cells was evaluated by the PrestoBlue cell viability assay. HUVEC (human umbilical vein endothelial cell line), HEK-293T (human embryonic kidney 293 cell line), RD (human rhabdomyosarcoma cell line), HepG2 (human liver cancer cell line), or A549 (human lung adenocarcinoma epithelial cell line) cells were incubated with GNS/Alg-NGs-270 (0.1 mg/mL to 1.0 mg/mL) for 72 h. As a result, FIG. 22A showed higher than 90% cell viability for all cells, indicating that GNS/Alg-NGs-270 displayed negligible cytotoxicity toward mammalian cells. The live/dead cell viability staining (calcein-AM/EthD-1) assay further demonstrated the low cytotoxicity of GNS/Alg-NGs-270, as evidenced by the fact that green fluorescent cells predominating in the population (FIGS. 22B and 22C). Furthermore, in vitro hemolysis assay results (FIG. 22D) showed no significant hemolysis in RBCs after incubation with GNS/Alg-NGs-270 (0.1 mg/mL to 1.0 mg/mL), indicating that GNS/Alg-NGs-270 was a safe injectable anticoagulant.

Example 6: Effects of GNS/Alg-NGs in the Animal Model of Tail Bleeding Assay In this example, the antihemostatic effect of GNS/Alg-NGs-270 was evaluated in vivo in rats by measuring the tail-bleeding time, at an applied dose of 0.50 mg/kg. Under the same conditions, the bleeding time of rats treated with PBS (as a control) and enoxaparin were 422±27 second (s) and 1392±164 s (n=20), respectively, whereas in GNS/Alg-NGs-270-treated rats, it was as long as 1831±152 s (n=20) (FIG. 23A). Obviously, the blood loss of GNS/Alg-NGs-270 treated rats (3218±317 mg) was significantly heavier (p<0.001) than that of rats treated with PBS (466±53 mg) and enoxaparin (1618±253 mg) (FIG. 23B).

Further, the plasma was collected from the rats after 30 min of intravenous administration of PBS, GNS/Alg-NGs-270, or enoxaparin for ex vivo analysis. Referring to 23C and 23D, the aPTT and PT assays of GNS/Alg-NGs-270 showed increases of 2.6-and 1.8-fold, respectively. On the contrary, enoxaparin showed a significantly shorter delay time in the aPTT and PT assays.

Despite enoxaparin being one of the most clinically used anticoagulants, it does have some important limitations, such as a narrow therapeutic window. Also, its use may result in low platelet count, excessive bleeding, allergic reaction, and bruising at higher doses. Moreover, enoxaparin diluted with a subcutaneous injectable solution and stored in cold and dark conditions only remains stable anticoagulation activity for up to 30 days. In sharp contrast, GNS/Alg-NGs-270 displayed even better and more stable anticoagulation activity than enoxaparin at the same concentrations, due to the high-affinity interaction with thrombin and mild interactions with other coagulant factors. The one-step synthesized self-functional GNS/Alg-NGs-270 were highly stable in both powder and solution form for over one year, and might act as an effective anticoagulant and antioxidant (data not shown). Moreover, the GNS/Alg-NGs also had antioxidant activity, which reduced ROS levels and stress, and may prevent cardiovascular diseases (CVDs) during therapy.

Figure 24:
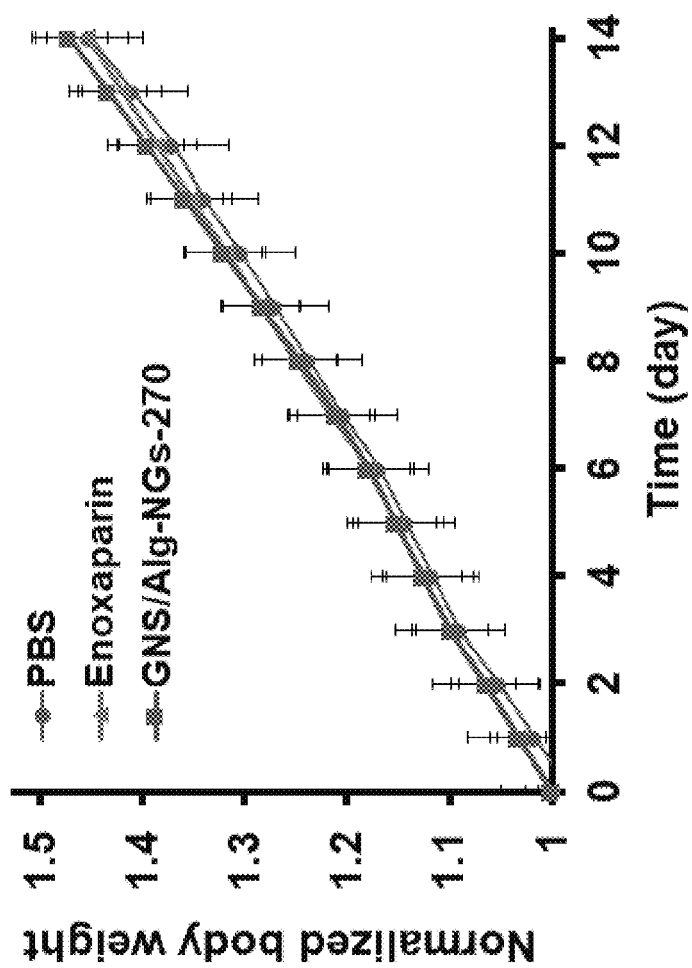
FIG. 24 shows the normalized body weight of male Sprague-Dawley rats within 14 days after the intravenous (IV) injection of GNS/Alg-NGs in the tail bleeding experiment.

In addition, the rats treated with GNS/Alg-NGs-270 did not show any weight change after 14 days of administration (FIG. 24). They also survived for 3 months and showed normal behavior during this time (data not shown). GNS/Alg-NGs-270, at a dose of only 0.50 mg/kg bodyweight of the rat, intravenously (IV) administered into the tail vein showed no significant in vivo toxicity. Therefore, biocompatible GNS/Alg-NGs were a great candidate for biomedical applications, such as prevention of thrombosis, and even reduction of the risk of CVD.

From the above, the experiments indicate that the graphene-like nanosheet-embedded non-sulfated polyphenolic polysaccharide nanogels, e.g., GNS/Alg-NGs-270, may be synthesized from sodium alginate by dry heating, e.g., at 270° C. In contrast to the parent molecule, sodium alginate, the GNS/Alg-NGs exhibit excellent anticoagulant and antioxidant activities. The GNS/Alg-NGs comprise or consist of GNS embedded in nanogels with polyphenolic structures that form through dehydration, condensation, and mild carbonization. The heating of sodium alginate causes the cross-linking of linear polymers through condensation reactions to form a gel matrix. Also, mild aromatization during the controlled heating results in the formation of polyphenolic structures, wherein some of the structural properties of alginate are preserved. As revealed by the TEG analysis, GNS/Alg-NGs have better anticoagulant efficiency than the sulfated polysaccharide, fucoidan, which itself is known to have great potential as an anticoagulant drug for the prevention and treatment of thromboembolic diseases. Therefore, the GNS/Alg-NGs of the present disclosure have promising potential for the replacement of conventional anticoagulants used for in vitro diagnostic tests as a cost-effective, safe, and viable drug.

There is an unmet need for nanodrugs made by simple synthesis procedures. The GNS/Alg-NGs disclosed herein meet the need via one-step synthesis, cost-effective materials, easy scale-up, and high reproducibility. Moreover, GNS/Alg-NGs are metal-free and carbon-based, and thus they are highly biocompatible, especially in comparison to recently reported metal-based anticoagulant nanomaterials. Several studies have also revealed a strong relationship between the successful treatment of CVDs and antioxidant and anticoagulation therapies. Since the GNS/Alg-NGs disclosed herein exhibit good anticoagulation activity, low cytotoxicity, high biocompatibility, and potential antioxidant activity, GNS/Alg-NGs may be developed as an anticoagulant or dietary supplement for the prevention of CVDs.

The present disclosure includes embodiments in which exactly one member of the group is present in, employed in, or otherwise relevant to a given product or process. The present disclosure also includes embodiments in which more than one, or all of the group members are present in, employed in, or otherwise relevant to a given product or process.

Those skilled in the art will recognize, or be able to ascertain by using no more than routine experimentation, many equivalents to the embodiments of the present disclosure which is described herein. The scope of the present disclosure is not intending to be limited to the embodiments disclosed, but rather includes all embodiments falling within the scope of the appended claims. In addition, many modifications will be appreciated to adapt a particular instrument, situation, or material to the teachings of the present disclosure without departing from the scope thereof.

What is claimed is:

1. An alginate nanogel, comprising a graphene-like nanosheet and a polysaccharide, wherein the graphene-like nanosheet comprises a carbonization product of at least a portion of the polysaccharide, and the graphene-like nanosheet is complexed with the polysaccharide to form a cross-linked supramolecular structure having a phenol functional group on a surface thereof, and wherein the alginate nanogel is formed by dry heating at 200° C. to 300° C.

2. The alginate nanogel of claim 1, wherein the polysaccharide is a salt of alginic acid.

3. The alginate nanogel of claim 2, wherein the salt of alginic acid is selected from the group consisting of sodium alginate, calcium alginate, magnesium alginate, and any combination thereof.

4. The alginate nanogel of claim 1, wherein the cross-linked supramolecular structure further has a functional group selected from the group consisting of hydroxyl, ester, carboxyl and any combination thereof on a surface thereof.

5. The alginate nanogel of claim 1, wherein the polysaccharide has a free end and a fixed end, and the fixed end of the polysaccharide is bonded to the surface of the graphene-like nanosheet.

6. The alginate nanogel of claim 1, which has a hydrodynamic diameter ranging from 20 nm to 490 nm.

7. The alginate nanogel of claim 6, which has a hydrodynamic diameter ranging from 40 nm to 250 nm.

8. The alginate nanogel of claim 1, which has a zeta potential ranging from −26.5 mV to −47.5 mV.

9. The alginate nanogel of claim 1, wherein the graphene-like nanosheet has lattice planes of (100) and (112) facets.

10. A method of preparing the alginate nanogel of claim 1, comprising carbonizing the polysaccharide by dry heating.

11. The method of claim 10, wherein the polysaccharide is a salt of alginic acid.

12. The method of claim 11, wherein the salt of alginic acid is selected from the group consisting of sodium alginate, calcium alginate, magnesium alginate, and any combination thereof.

13. The method of claim 10, further comprising dissolving the carbonized polysaccharide into water.

14. A method for preventing or treating a disease or a condition susceptible to amelioration by an anticoagulant or an antioxidant in a subject in need thereof, comprising administering to the subject a composition comprising the alginate nanogel of claim 1 and a pharmaceutically acceptable vehicle thereof.

15. The method of claim 14, wherein the disease or the condition susceptible to amelioration by the anticoagulant or the antioxidant is selected from the group consisting of thrombophilia, vascular thrombosis, pulmonary embolism, cardiac ischemia, ischemic stroke, cryptogenic stroke, embolic stroke of an undetermined source, myocardial infarction, pulmonary hypertension, and asthma.

* * * * *